(12) United States Patent
Morris et al.

(10) Patent No.: US 10,502,720 B2
(45) Date of Patent: Dec. 10, 2019

(54) METHODS FOR LIQUID CHROMATOGRAPHY CALIBRATION FOR RAPID LABELED N-GLYCANS

(71) Applicant: Waters Technologies Corporation, Milford, MA (US)

(72) Inventors: Michael F. Morris, Ashland, MA (US); Matthew A. Lauber, North Smithfield, RI (US); Darryl W. Brousmiche, Grafton, MA (US)

(73) Assignee: Waters Technologies Corporation, Milford, MA (US)

( * ) Notice: Subject to any disclaimer, the term of this patent is extended or adjusted under 35 U.S.C. 154(b) by 51 days.

(21) Appl. No.: 15/526,325

(22) PCT Filed: Nov. 12, 2015

(86) PCT No.: PCT/US2015/060326
§ 371 (c)(1),
(2) Date: May 11, 2017

(87) PCT Pub. No.: WO2016/077548
PCT Pub. Date: May 19, 2016

(65) Prior Publication Data
US 2017/0336368 A1 Nov. 23, 2017

Related U.S. Application Data

(60) Provisional application No. 62/079,460, filed on Nov. 13, 2014.

(51) Int. Cl.
*G01N 30/00* (2006.01)
*G01N 30/02* (2006.01)
(Continued)

(52) U.S. Cl.
CPC .......... *G01N 30/02* (2013.01); *B01D 15/305* (2013.01); *C07D 215/48* (2013.01); *C07H 15/26* (2013.01);
(Continued)

(58) Field of Classification Search
CPC .................................................... G01N 30/02
(Continued)

(56) References Cited

U.S. PATENT DOCUMENTS 2,016,962 A 10/1935 Flint et al.
4,003,912 A 1/1977 Franz
(Continued)

FOREIGN PATENT DOCUMENTS

CA 2475011 A1 8/2003
CN 1973047 A 5/2007
(Continued)

OTHER PUBLICATIONS

Ahn et al., Separation of 2-aminobenzamide labeled glycans using hydrophilic interaction chromatography columns packed with 1.7 μm sorbent. J Chrom B 2010; 878: 403-8.
(Continued)

*Primary Examiner* — Lyle Alexander
*Assistant Examiner* — Emily R. Berkeley

(57) ABSTRACT

Methods are provided for making rapid labeled dextran ladders and other calibrants useful in liquid chromatography. The methodologies include a two-step process comprising a reductive amination step of providing a reducing glycan and reacting it with a compound having a primary amine to produce an intermediate compound. The intermediate compound is then rapidly tagged with a rapid tagging reagent to produce the rapid labeled dextran ladder.

1 Claim, 12 Drawing Sheets

(51) Int. Cl.
*C07D 215/48* (2006.01)
*G01N 30/04* (2006.01)
*B01D 15/30* (2006.01)
*C07H 15/26* (2006.01)
*G01N 30/88* (2006.01)
*G01N 33/68* (2006.01)
*G01N 30/62* (2006.01)

(52) U.S. Cl.
CPC ............. *G01N 30/04* (2013.01); *G01N 30/88* (2013.01); *G01N 33/6842* (2013.01); *G01N 2030/027* (2013.01); *G01N 2030/047* (2013.01); *G01N 2030/626* (2013.01); *G01N 2030/8836* (2013.01); *G01N 2400/00* (2013.01); *G01N 2440/38* (2013.01)

(58) Field of Classification Search
USPC .......................................................... 436/14
See application file for complete search history.

(56) References Cited

U.S. PATENT DOCUMENTS

| | | | |
|---|---|---|---|
| 4,138,398 | A | 2/1979 | Richter et al. |
| 5,296,599 | A | 3/1994 | Cohen et al. |
| 6,245,478 | B1 | 6/2001 | Uetani et al. |
| 6,632,629 | B2 | 10/2003 | Yang et al. |
| 7,148,069 | B2 | 12/2006 | Miyano et al. |
| 7,494,815 | B2 | 2/2009 | Shimbo et al. |
| 8,124,792 | B2 | 2/2012 | Baginski |
| 8,445,292 | B2 | 5/2013 | Baginski |
| 9,658,234 | B2 | 5/2017 | Miyano et al. |
| 2001/0026929 | A1 | 10/2001 | Yang et al. |
| 2005/0079624 | A1 | 4/2005 | Miyano et al. |
| 2005/0158708 | A1 | 7/2005 | Alroy et al. |
| 2006/0004220 | A1 | 1/2006 | Hamprecht et al. |
| 2006/0035304 | A1 | 2/2006 | Lebrilla et al. |
| 2006/0286673 | A1 | 12/2006 | Miyano et al. |
| 2008/0241856 | A1 | 10/2008 | Wong et al. |
| 2008/0315084 | A1 | 12/2008 | Yamada et al. |
| 2009/0258437 | A1 | 10/2009 | Baginski |
| 2011/0171736 | A1 | 7/2011 | Agnew et al. |
| 2012/0107942 | A1 | 5/2012 | Baginski |
| 2012/0165370 | A1 | 6/2012 | Tang et al. |
| 2014/0179011 | A1 | 6/2014 | Brousmiche et al. |
| 2014/0350263 | A1 | 11/2014 | Brousmiche et al. |
| 2015/0346194 | A1 | 12/2015 | Magnelli et al. |

FOREIGN PATENT DOCUMENTS

| | | |
|---|---|---|
| CN | 103842818 A | 6/2014 |
| CN | 103877748 A | 6/2014 |
| CN | 104024849 A | 9/2014 |
| EP | 0533200 A1 | 3/1993 |
| EP | 0671401 A1 | 9/1995 |
| EP | 1475632 A1 | 11/2004 |
| EP | 1750126 A1 | 2/2007 |
| JP | S60186502 A | 9/1985 |
| JP | H10306075 A | 11/1998 |
| JP | H1180107 A | 3/1999 |
| JP | 2000510854 A | 8/2000 |
| JP | 2006523305 A | 10/2006 |
| JP | 2008539413 A | 11/2008 |
| JP | 2015091953 A | 5/2015 |
| WO | 2004027388 A2 | 4/2004 |
| WO | 2003069328 A | 6/2005 |
| WO | 2005116629 A1 | 12/2005 |
| WO | 2006114663 A1 | 11/2006 |
| WO | 2007069591 A1 | 6/2007 |
| WO | 2009070233 A1 | 6/2009 |
| WO | 2009100155 A1 | 8/2009 |
| WO | 2011038873 A1 | 4/2011 |
| WO | 2011146594 A2 | 11/2011 |
| WO | 2013025527 | 2/2013 |
| WO | 2013025527 A1 | 2/2013 |
| WO | 2013049622 | 4/2013 |
| WO | 2013049622 A1 | 4/2013 |
| WO | 2013084236 A1 | 6/2013 |
| WO | 2016069764 | 5/2016 |
| WO | 2016069764 A1 | 5/2016 |

OTHER PUBLICATIONS

Campbell et al., GlycoBase and autoGU: tools for HPLC-based glycan analysis. Bioinformatics 2008; 24 (9): 1214-6.
Guile et al., A Rapid High-Resolution High-Performance Liquid Chromatographic Method for Separating Glycan Mixtures and Analyzing Oligosaccharide Profiles. Analytical Biochemistry 1996; 240: 210-26.
International Search Report and Written Opinion, dated Feb. 2, 2016, PCT/US15/60326. 8 pages.
Harvey, David J., "Identification of protein-bound carbohydrates by mass spectrometry" Proteomics 1:311-328, (2001).
Kimzey, M., et al., "Development of an Instant Glycan Labeling Dye for High Throughput Analysis by Mass Spectrometry", Prozyme Advancing Glycosciences [online] (2015) [retrieved on Jun. 5, 2019]. Retrieved from Internet URL: https://www.europa-bioproducts.com/pdf/IPC_Glycan-Labeling-Dye-2015_handout_v3_r2.pdf, 4 pages.
Chezal, Jean-Michel et al. "Evaluation of Radiolabeled (Hetero)Aromatic Analogues of N-(2-diethylaminoethyl)-4-iodobenzamide for Imaging and Targeted Radionuclide Therapy of Melanoma" J. Med. Chem. 2008, 51, 3133-3144.
International Search Report and Written Opinion, dated Apr. 27, 2017, for International Application No. PCT/US2017/014790, 6 pages.
Mazzocchi, Paul H. et al., "A Photochemical Route to Pyrrolo[1,4]Benzodiazepine Antitumor Antibiotics" Heterocycles 1985, 1603-1606, vol. 23, No. 7.
Holmes, Darren L., et al., "Solid-Phase Synthesis of Artificial beta-Sheets" J. Am. Chem. Soc. 1997, 119, 7665-7669.
Hossler et al., Optimal and Consistent Protein Glycosylation in Mammalian Cell Culture, Blycobiology 2009: 19:936-49.
Anumula, et al., High Resolution and High Sensitivity Methods for Oligosaccharide Mapping and Characterization by Normal Phase High Performance Liquid Chromatography Following Derivitization with Highly Flourescent Anthranilic Acid, Glycobiology 1998: 8:685-94.
Marino, et al., A Systematic Approach to Protein Glycosylation Analysis: A Path Through the Maze, Nature Chemical Biology 2010: 6:713-23.
Suzuki, et al, Comparision of the Sensitivities of Various Derivatives of Oligosacchardies in LC/MS with Fast Atom Bombardment and Elecgtrospray Ionization Interfaces, Anal Chem 1996: 68:2073-83.
Yu, et al., A Rapid Sample Preparation Method for Mass Spectrometric Characterization of N-linked Glycans, Rapid Comm Mass Spectrometry 2005; 19:331-36.
Klapoetke, et al., The Evaluation of a Novel Approach for the Profiling and Identification of N-linked Glycans With a Procainamide Tag by HPLC With Fluorescent and Mass Spectrometric Detection, J. Pharmaceutical and Biomedical Anal 2010; 53:315-24.
Nimura, et al., Activated Carbamate Reagent as Derivatizing Agent for Amino Compounds in High-Performance Liquid Chromatography, Analytical Chemistry 58(12):2372-75 (1986).
Takeda, et al., Convenient Methods for Syntheses of Active Carbamates, Ureas and Nitrosoureas Using N,N'-Disuccinimido Carbonate (DSC), Tetrahedron Lett 1983; 24:4569-72.
Wada, et al., Comparison of the Methods for Profiling Glycoprotein Glycans—HUPO Human Disease Glycomics/Proteome Initiative Multi-Institutional Study, Glycobiology 2007; 17:411-22.
Wuhrer, et al., Nano-Scale Liquid Chromatography-Mass Spectrometry of 2-Aminobenzamide-Labeled Oligosaccharides at Low Femtomole Sensitivity, Int J Mass Spectrom 2004; 232:51-57.
Heinze-Krauss, et al., Structure-Based Design of B-Lactamase Inhibitors. 1. Synthesis and Evaluation of Bridged Monobactams, J Med Chem 1998; 41:3961-71.

(56) References Cited

OTHER PUBLICATIONS

Isbell, et al., Effect of pH in the Mutarotation and Hydrolysis of Glycosylamines, JAGS 1950; 72:1043-4.
Tarentino et al., 2-Iminothiolane: A Reagent for the Introduction of Sylphydryl Groups into Oligosaccharides Derived from Asparagine-Linked Glycans, Glycobiology 1993; 3:279-85.
Saurina et al., Chromatographic Determination of Amino Acids by Pre-Column Derivatization Using 1,2-Napthoquinone-4-Sulfonate as Reagent, J Chromatogr A 1996; 740:21-30.
Piepponen et al., Rapid and Sensitive Step Gradient Assays of Glutamate, Glycine, Taurine and y-Aminobutyric Acid by High-Performance Liquid Chromatography-Fluorescence Detection with o-Phthalaldehyde-Mercaptoethanol Derivatization With an Emphasis on Microdialysis Samples, J Chromatogr B 2001; 757:277-83.
Black et al., Simple, Rapid, and Highly Efficient Separation of Amino Acid Phenylthiohydantoins by Reversed-Phase High-Performance Liquid Chromatography, Anal Biochem 1982; 121:281-85.
Casoli et al., Use of High-Performance Liquid Chromatography for the Determination of Amino Acids in Sparkling Wines, Am J Enol Vitic 1982; 33:135-39.
Liu et al., Determination of Submicromolar Concentrations of Neurotransmitter Amino Acids by Fluorescence Detection Using a Modification of the 6-Aminoquinolyl-N-Hydroxysuccinimidyl Carbamate Method for Amino Acid Analysis, J Chromatogr A 1998; 828:383-95.
Park et al., Regioselective Covalent Modification of Hemoglobin in Search of Antisickling Agents, J Med Chem 2003; 46:936-53.
Saurina et al., Determination of Amino Acids by Ion-Pair Liquid Chromatography With Post-Column Derivatization Using 1,2-Naphthoquinone-4-Sulfonate, J Chromatogr A 1994; 676:311-19.
Schmidt et al., Amino Acid Profiling of Protein Hydrolysates Using Liquid Chromatography and Fluorescence Detection, J Liq Chromatogr 1979; 2:1031-45.
Van Wandelen et al., Using Quaternary High-Performance Liquid Chromatography Eluent Systems for Separating 6-Aminoquinolyl-N-Hydroxysuccinimidyl Carbamate-Derivatized Amino Acid Mixtures, J Chromatogr A 1997; 763:11-22.
Wei et al., Study on N-Hydroxyphthalimide as Blocking Agent for Isocyanates, J Appl Polym Sci 2002; 84:1346-52.
Kurita et al., Synthesis and Properties of Polyurethanes Derived from bis-N-Hydroxyimides and Diisocyanates, J Polym Sci 1979; 17:1619-29.
International Search Report and Written Opinion, PCT/US2012/057996 dated Jan. 31, 2013.
Vasilevich et al, Conversion of O-Succinimidyl Carbamates to N-(O-Carbamoyl)-Succinmonoamides and Ureas: Effects of N-Substituents and Reaction Conditions on the Reaction Pathway, Tetrahedron Lett 2002; 43:6649-52.
Guichard et al,. Preparation of O-Succinimidyl-2-(tert-Butoxycarbonylamino)ethylcarbamate Derivatives from Beta-Amino Acids. Application to the Synthesis of Urea-Containing Pseudopeptides and Oligoureas, J Org Chem 1999; 64:8702-5.
Cooper et al., LC-MS/MS Analysis of AccQ-Tag Derivatised Amino Acids, Micromass Application Brief, Sep. 2000 and Jun. 2000.
Cohen, Compositional Protein Analysis Using 6-Aminoquinolyl-N-Hydroxysuccinimidyl Carbamate, a Novel Derivatization Reagent, Techniques in Prat Chem IV 1993; 289-298.
De Antonis et al., High-Performance Liquid Chromatographic Analysis of Synthetic Peptides Using Derivatization with 6-Aminoquinolyl-N-Hydroxysuccinimidyl Carbamate, Anal Biochem 1994; 223:191-7.
Liu et al., Femtomole Peptide Mapping by Derivatization, High-Performance Liquid Chromatography, and Fluorescence Detection, Anal Biochem 2001; 294:7-18.
Cohen et al., Synthesis of a Fluorescent Derivatizing Reagent, 6-Aminoquinolyl-N-Hydroxysuccinimidyl Carbamate, and Its Application for the Analysis of Hydrolysate Amino Acids via High-Performance Liquid Chromatography, Anal Biochem 1993; 211 : 279-87.
Higashi et al., Derivatization of Neutral Steroids to Enhance Their Detection Characteristics in Liquid Chromatography-Mass Spectrometry, Anal Bioanal Chem 2004; 378:875-882.
Hochleitner et al., Determination of the Stoichiometry of Protein Complexes Using Liquid Chromatography with Fluorescence and Mass Spectrometric Detection of Fluorescently Labeled Proteolytic Peptides, Proteomics 2004; 4:669-676.
Schmeer et al., Compositional Analysis of the Phenylthiocarbamyl Amino Acids by Liquid Chromatography-36 Atmospheric Pressure Ionization Mass Spectrometry with Particular Attention to the Cyst(e)ine Derivatives, J of Chromatography 1995; 691 :285-99.
Martinez-Force et al., Separation of O-Phthalaldehyde Derivatives of Amino Acids of the Internal Pool of Yeast by Reverse-Phase Liquid Chromatography, Biotech Tech 1991; 5(3):209-14.
Block, The Use of 6-Aminoquinolyl-N-Hydroxy Succinimidyl Carbamate Derivatives for HPLC/MS Analysis of Amino Acids, AMD35 Waters Alliance LC/MS System 2000.
Cooper et al., LC-MS/MS Analysis of AccQ-Tag Derivatised Amino Acids, Micromass UK Limited 2000.
Block et al., Abstract 2050P: HPLC-MS Analysis of Amino Acids, Pittsburgh Conference, Mar. 1999.
Block et al., Poster 2050P: HPLC/MS Analysis of Amino Acids: The Use of 6-Aminoquinolyl-N-Hydroxy-Succinimidyl Carbamate Derivatives, Pittsburgh Conference, Mar. 1999.
Cooper et al., LC-MS-MS Analysis of Amino Acids Using AccQ-Tag derivatisation, Application Brief AB25, Micromass Jun. and Sep. 2000.
Block, Presentation: LC/MS Application Notes: The Use of 6-Aminoquinolyl N Hydroxy Succinimidyl Carbamate Derivatives for HPLC/MS Analysis of Amino Acids, Pittsburgh Conference, Mar. 1999.
Field, B., et al., Chromatography Forum: LC-MS & GC-MS Archives: AAA LC-MS, http://www.lcresources. com/d iscus/messages/5135/3143. html?MondayApril 1420030826pm Jan.-Apr. 2003.
Liu, Hongji, et. al.; "Homogeneous Fluorescent Derivatization of Large Proteins"; Journal of Chromatography A, 927 2001) pp. 77-89.
Ahn et al., "Separation of 2-aminobenzamide labeled glycans using hydrophilic interaction chromatography columns packed with 1.7 µm sorbent", J Chrom B 878:403-8 (2010).
Campbell et al., "GlycoBase and autoGU: tools for HPLC-based glycan analysis", Bioinformatics 24(9):1214-6 (2008).
Guile et al., "A Rapid High-Resolution High-Performance Liquid Chromatographic Method for Separating Glycan Mixtures and Analyzing Oligosaccharide Profiles", Analytical Biochemistry 240: 210-26 (1996).
Yu, N-linked Glycan Characterization and Profiling: Combining the Power of Accurate Mass, Reference Glucose Units, and UNIFI Software for Confident Glycan Assignments. Waters. Application Note. 2013.
Dextran Calibration Ladder Standard. Waters. 2012.
Dextran Calibration Ladder. Waters. Product Solution. 2013.
International Search Report and Written Opinion for application No. PCT/US/15/60326, dated Feb. 2, 2016, 6 pages.
Communication of a notice of opposition for EP Patent No. 2761296 dated Jun. 5, 2018.
Response to notice of opposition for EP Patent No. 2761296 filed Oct. 19, 2018.
Harvey, D., "Identification of protein-bound carbohydrates by mass spectrometry" Proteomics pp. 318-319 (2001).
Ullmer, Roman, et. al.; "Derivatization by 6-aminoquinolyl-N-hydroxysuccinimidyl Carbamate for Enhancing the Ionization Yield of Small Peptides and Glycopeptides in Matrix-Assisted Laser Desorption/Ionization and Electrospray Ionization Mass Spectrometry"; Rapid Communications in Mass Spectrometry (2006) pp. 1469-1479.
Kinzel, Olaf, et al.; "Identification of MK-5710 ((8aS)-8a-methyl-1,3-dioxo-2-((1S,2R)-2-phenylcyclopropyl]-N-(1-phenyl-1 H-pyrazol-5-yl)hexahydro-imidazo [1,5-a]pyrazine-7(1 H)-carboxamide), a potent smoothened antagonist for use in Hedgehog pathway dependent malignancies, Part 2"; Bioorganic & Medicinal Chemistry Letters; vol. 21 (2011) pp. 4429-4435.

(56) References Cited

OTHER PUBLICATIONS

European Search Report and Written Opinion dated Aug. 26, 2014 regarding patent application No. EP 12836127.6, 5 pages.
European Search Report and Written Opinion dated Feb. 2, 2016 regarding patent application No. EP 15180680.9, 7 pages.
Extended European Search Report, EP 12836127.6, dated Aug. 26, 2014.
International Preliminary Report on Patentability, PCT/US2012/057996, dated Apr. 1, 2014.
Supplementary European Search Report, EP12836127.6 dated Sep. 12, 2014 and Response dated Mar. 19, 2015.
Briggs, J. B., et al., "An analytical system for the characterization of highly heterogeneous mixtures of N-linked oligosaccharides," Analytical Biochemistry, 389:40-51, Jan. 15, 2009.

METHODS FOR LIQUID CHROMATOGRAPHY CALIBRATION FOR RAPID LABELED N-GLYCANS

CROSS REFERENCE TO RELATED APPLICATIONS

None.

BACKGROUND OF THE INVENTION

Hydrophilic interaction chromatography ("HILIC") separation coupled with fluorescence detection in UPLC platforms can be used to resolve complex N-linked glycan populations due to the ability to separate both neutral and charged glycans in a single chromatographic run. Because of the heterogeneity, isomerization and anomericity of glycans, elucidating the structure of complex N-linked glycans can be a significant analytical challenge. A dextran ladder can be used to calibrate hydrophilic interaction chromatography ("HILIC") separations of glycans and convert peak retention times into glucose unit ("GU") values. Each individual glycan structure has a GU value which is directly related to its linkages and its constituent monosaccharides. The GU value can be used to predict structures because each glycan structural component contributes in a specific way to the GU value of a given glycan.

As such, the elution times of glycans can be expressed in glucose units by reference to a separation calibrant, such as one based on a dextran ladder. A dextran ladder can be used to calibrate the liquid chromatography ("LC") runs against day-to-day or system-to-system changes. A GU value can be calculated by fitting a fifth order polynomial distribution curve or a cubic spline fit to the retention times of the dextran ladder. Then, using this curve, GU values can be assigned from the retention times observed in a test sample. The GU values for N-glycans can be reproducible, with inter-column standard deviations less than 0.3. This allows direct comparison with database values collected from a range of instruments over a period of time. Having GU values, databases of glycans stored in values of GU can be interrogated to aid in elucidating the potential glycan structures existing with a glycan population.

Furthermore, even when comparing different approaches for tagging, it can be seen that the labeled N-glycans are resolved by the HILIC separation into very similar profiles. It is not a trivial task to produce a dextran ladder that is appropriate for use with glycans that are rapidly labeled with a rapid tagging reagent. Dextran is a saccharide comprised of a reducing, aldehyde terminus, different than N-glycosylamines which are released via enzymatic deglycosylation of N-glycosylated proteins. Unlike the latter, dextran cannot therefore be modified with a rapid tagging reagent that targets amine nucleophiles. The dextran cannot be rapidly labeled because the saccharide does not contain an appropriate nucleophile. A need exists, as a result, for methods of calibrating the liquid chromatography processes with a standard that has the same optical and/or other physiochemical properties as the rapid labeled N-glycan.

SUMMARY OF THE INVENTION

Methods of making a rapid labeled dextran ladder and other calibrants useful in liquid chromatography are provided herein. The methods comprise the steps of providing a reducing glycan having an aldehyde group and reacting the reducing glycan with a compound having a primary amine to produce an intermediary compound. The intermediary compound is rapidly labeled with the rapid tagging reagent to produce a rapid labeled dextran ladder having substantially identical optical properties as a rapid labeled N-glycan produced by rapid tagging of the N-glycan with the rapid tagging reagent. Calibrants are also provided herein of the structural formula:

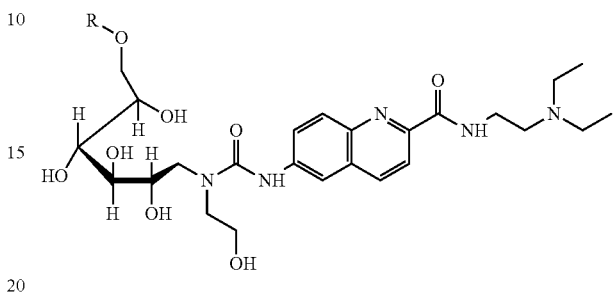

wherein R is a glucose unit or a monosaccharide unit. The methods provided herein are useful for rapid tagging or dual tagging compounds containing an aldehyde group.

DETAILED DESCRIPTION

Figure 1:
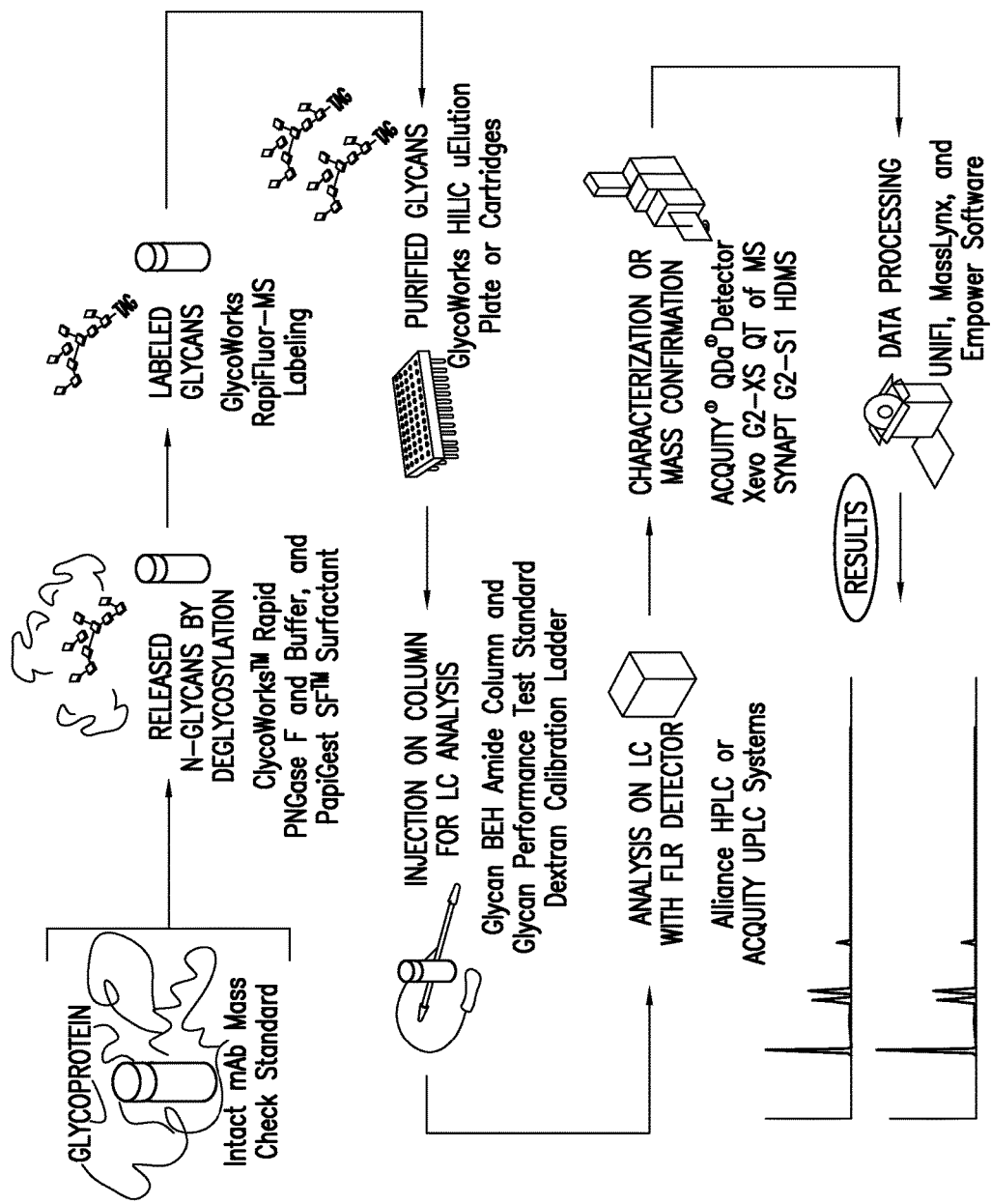
FIG. 1 shows an embodiment of workflow for preparing a rapid labeled N-glycan.

In the manufacturing of biopharmaceuticals, glycosylation profiles of biological samples are often assessed through an analysis of released glycans. These samples, however, are often prepared with techniques that are time-consuming or ones that can lead to a compromise in mass spectrometry ("MS") sensitivity. Enzymatic release and rapid labeling of N-glycans can address many shortcomings and provide higher throughput of N-glycan sample preparation and enable improved sensitivity for glycan detection. For example, as described herein, with an enzymatic release and rapid labeling of N-glycans, glycoproteins can now be deglycosylated in as low as 10 minutes to produce N-glycans which are then rapidly reacted with rapid tagging reagents. The resulting labeled glycans are then extracted from the labeling reaction byproducts by an SPE method to facilitate analysis of samples.

The N-glycan profile of a biopharmaceutical is a critical quality attribute because it can be a measure of efficacy, safety, and manufacturing conditions. Therefore, approaches for glycan analysis of clinical and commercial bio-therapeutic formulations require high sensitivity. Additionally, when the analysis is performed, rapid turnaround times and high throughput capacity can expedite product development.

Most analytical strategies for evaluating N-glycans from glycoproteins involve deglycosylation via PNGase F and the labeling of the resulting N-glycans with a chemical moiety that imparts a detectable attribute. In one approach described herein, labeled glycans are separated by hydrophilic interaction chromatography ("HILIC") and detected by fluorescence ("FLR") and mass spectrometry ("MS").

Furthermore, we previously developed a sample preparation solution that enables FLR and MS sensitivity for glycan detection while improving throughput of N-glycan sample preparation. We have developed rapid tagging reagents which can be synthesized to rapidly react with N-glycans upon their release from glycoproteins. (Brousmiche, et al., U.S. Published Patent Application No. 2014/0350263, filed Aug. 13, 2014, ¶¶[0008]-[0022], [0047]-[0050], [0053]-[0182], [0191], [0228] and [0230]-[0316], incorporated herein by reference). By utilizing the rapid tagging reagent, within a 5 minute reaction, N-glycans can be labeled. The rapid tagging reagents utilized herein comprise an N-hydroxysuccinimide (NHS) carbamate rapid tagging group, an efficient quinoline fluorophore, and a highly basic tertiary amine for enhancing ionization and are exemplified in Table 1 below.

TABLE 1

Exemplary Rapid Tagging Reagents

| Rapid Tagging Reagent No. | Labeling Reagent Structure | Chemical Name | Other Reagent Reference Names |
|---|---|---|---|
| 1 | | 2,5-dioxopyrrolidin-1-yl (2-((2-(diethylamino)ethyl)carbamoyl)quinolin-6-yl)carbamate | RapiFluor-MS or RFMS |
| 2 | | 2,5-dioxopyrrolidin-1-yl (4-((2-(diethylamino)ethyl)carbamoyl)phenyl)carbamate | |
| 3 | | 2,5-dioxopyrrolidin-1-yl quinolin-6-ylcarbamate | |
| 4 | | 2,5-dioxopyrrolidin-1-yl methylcarbamate | |
| 5 | | 2,5-dioxopyrrolidin-1-yl (4-carbamoylphenyl)carbamate | IAB, or Instant AB |

In the present methods, a reducing saccharide is labeled (tagged) via reductive amination and the resulting secondary amine containing saccharide is rapidly tagged with a rapid tagging reagent. The methodologies presented herein can be used in tagging or dual tagging any compounds containing an aldehyde.

To further accelerate the preparation of N-glycans, use of the rapid tagging reagent can be directly integrated with the PNGase F deglycosylation procedure which further involves a surfactant and a HILIC μElution solid phase extraction ("SPE") clean-up procedure to provide a quantitative recovery of the released and labeled glycans having the added benefit of no solvent dry-down step prior to the liquid chromatography ("LC") analysis of samples.

Example 1

Rapid Preparation of Released N-Glycans HILIC Analysis Using Rapid Tagging Reagents In this example, we describe how to prepare tagged (also referred to herein as "labeled") N-glycans, from glycoprotein to analysis ready sample, in 30 minutes with complete deglycosylation. Our process is a streamlined protocol that can be facilitated by a kit known as the GLYCOWORKS™ RAPIFLUOR-MS™ N-glycan Kit. Sensitivity for labeled N-glycans can be at least 2 and 100 fold increases to previous fluorescence and MS detection and can provide accurate profiling based on robust solid phase extraction ("SPE") to neutralize tetrasialylated N-glycans. Lauber, M. et al., *Rapid Preparation of Released N-Glyans for HILIC Analysis Using a Labeling Reagent that Facilitates Sensitive Fluorescence and ESI-MS Detection*, Anal. Chem. 2015, 97, 5401-5409, incorporated herein by reference.

The rapid tagging reagent facilitating our N-glycan analysis was synthesized based on rational design considerations which afford rapid labeling kinetics, high fluorescence quantum yield, and significantly enhanced MS detectability. N-glycan sample preparation can be dependent on reductive amination of aldehyde terminated saccharides. In this process, glycans are reductively aminated in anhydrous conditions in order to minimize desialylation. The sample preparation transitions from aqueous to anhydrous conditions. On the other hand, by utilizing the rapid tagging reagent, reductive amination can be eliminated through an aqueous rapid tagging reaction.

If not labeled by a rapid tagging reaction, glycans can indeed be labeled at their reducing end using reductive amination. In this reaction, a tagging reagent containing a primary amine reacts in a condensation reaction with the aldehyde group of the glycan, resulting in an imine or Schiff base, which is reduced by a reducing agent to yield a secondary amine. The reaction is often performed in dimethyl sulfoxide containing acetic acid, but alternative approaches using tetrahydrofuran and methanol have been described. Examples of an amine (also referred to herein as primary amine or compound having a primary amine) include ethanol amine, propylamine, aminobenzamide, peptides with a free amino terminus (as shown in example 5 herein), N,N-dimethylehtylene diamine, amino anthracene and amino biotin. An advantage of this labeling approach is the stoichiometric attachment of one label per glycan, allowing a direct quantitation based on fluorescence or UV-absorbance intensity.

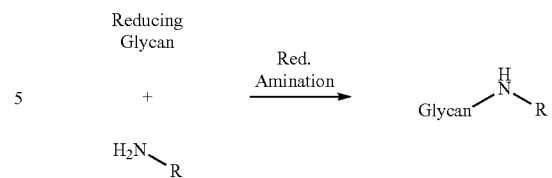

Rapid tagging of glycans can, alternatively, be readily adopted in the laboratory with the GLYCOWORKS™ RAPIFLUOR-MS™ N-glycan Kit described herein, purposefully designed to remove the bottlenecks from all aspects of N-glycan sample preparation. As shown in FIG. 1 below, the optimized N-glycan sample preparation workflow requires three steps: (1) deglycosylation to release glycans from a glycoprotein; (2) labeling to impart a detectable chemical entity to glycans; and (3) a clean-up step to remove potential interferences from the sample. These glycans are then rapidly reacted with one or more of the rapid tagging reagents and are thereby labeled with a tag comprised of an efficient fluorophore and a highly basic tertiary amine that yields enhanced sensitivity for both fluorescence and MS detection. A depiction of the structure of a rapid labeled glycan is shown immediately below. It is worth noting the rapid labeled glycans have a particularly unique linkage moiety, one that is distinct from the secondary amine linkage that comes from reductive amination reactions. Rapid labeled N-glycans will contain neutral (not acidic) urea linkages. This can impact the physicochemical characteristics and/or properties of the rapid labeled glycans, including their chromatographic retention and their fluorescence properties and other physiochemical properties such as isoelectric point ("pI"), acidity, basicity, hydrophobicity, hydrophilicity, ability to chelate metals, UV absorbance, fluorescence, absorbance in the visible spectrum, colorimetric changes, molecular size, affinity to interacting with binding partners (i.e. biotinylated residues to avidin or streptavidin, epitopes to paratopes), reduction/oxidation potential, propensity for crosslinking, cleavability (chemical and thermal), and polymeric substituents of varying length (i.e. poly ethylene glycol (PEG) 4 repeats, PEG 40 repeats).

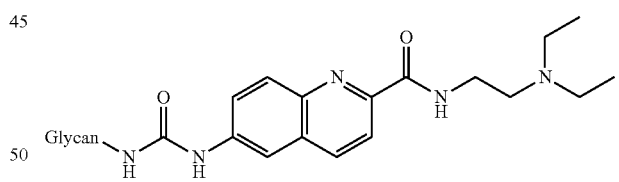

As used herein, the marks GLYCOWORKS™ and RAPIFLUOR-MS™ are owned by applicant, Waters Technologies Corporation. The mark GLYCOWORKS™ is used in connection with sample preparation kits for laboratory use comprising biological standards, sample preparation device, and disposable cartridges and chemical reagents for preparing samples for chromatography and mass spectrometry. Similarly, the mark RAPIFLUOR-MS™ is used in connection with chemical reagents for preparing samples for chromatography and mass spectrometry and in connection with sample preparation kits for laboratory use comprising biological standards, sample preparation devices, and disposable cartridges.

As such the GLYCOWORKS™ RAPIFLUOR-MS™ N-glycan Kit can be used for the fast enzymatic release and rapid labeling of N-glycans. This protocol has been validated using monoclonal antibodies and has also been tested to perform for a wide range of other N-linked glycoproteins. This sample preparation kit uses optimized deglycosylation conditions and reagents for fast release. The kit can include a rapid label reagent described U.S. Published Patent Application No. 2014/0350263, filed Aug. 13, 2014, ¶¶[0008]-[0022], [0047]-[0050], [0053]-[0182], [0191], [0228] and [0230]-[0316], incorporated herein by reference, and is designed to provide both the benefits of sensitive fluorescence detection as well as having appropriate signal intensity for mass detection.

As described herein, characterization and monitoring of N-glycosylation of proteins is significant in the detection of disease states and the manufacturing of biopharmaceuticals. Glycosylation profiles are most often assessed by means of released glycan analyses, wherein samples are often prepared by techniques that are notoriously time-consuming or lead to compromises in MS sensitivity. With the development of the GlycoWorks RapiFluor-MS N-Glycan Kit described herein, these shortcomings have been addressed by enabling unprecedented sensitivity for glycan detection while also improving the throughput of N-glycan sample preparation.

Equally important as the efficiency and sensitivity gains afforded by this new sample preparation approach, and the associated methodologies, is its robustness and its ability to produce results consistent with historical N-glycan profiling. Furthermore, glycan data generated can be used to interrogate glycan databases but first require conversion into a standardized valve called a Glucose Unit ("GU") value. Hence, another benefit of implementing a calibration standard is the ability to convert existing glycan data into a format that makes exploration of glycan databases possible. The converted data can be used in a discovery process, where samples of unknown glycan composition are under investigation. Once glycans are converted to GU values, users are able to interrogate online databases to gain insight into the potential glycan structures that may exist in their samples, potentially reducing the time required to perform a typical characterization. In liquid chromatography, calibration is performed frequently, sometimes as often as after every separation of the glycan mixture.

To detect fluorescent ("FLR") labeled glycans, hydrophilic interaction liquid chromatography ("HILIC") coupled with fluorescent detection can be used. For separation processing and in comparison to certain conventional high performance liquid chromatography ("HPLC") methods, an ethylene bridged glycan column (herein after referred as "BEH glycan column" or "BEH column") operating in HILIC mode can provide improvements in peak resolution with the ability to separate both neutral and acidic glycans. The BEH glycan column enables and produces reproducible glycan separation data and in less time spent for method optimization.

BEH columns utilize hybrid-silica BEH, bridged technology particles functionalized with a stable, amide-containing species. BEH technology has given rise to numerous particle size stationary phases ranging from 1.7 to 5 µm diameters to provide a bridge between HPLC and ultra-performance liquid chromatography ("UPLC") technology platforms. BEH particles offer peak shape and efficiency for basic analytes, a rational array of chromatographic selectivity and improvements in chemical stability at mobile phase extremes, particularly at elevated pH. The resolving power of these columns is due in part to porous particles with an optimal concentration of amide ligands for associated applications. The column can be optimized for use with either a UPLC or HPLC system having fluorescence ("FLR") detection for separating the released and labeled N-linked glycans from various bio-therapeutics, and achieve HILIC-based separations of both neutral and charged labeled glycan species.

In order to take full advantage of the BEH glycan column, or simply any HILIC-based profiling of glycans, a dextran calibration ladder (hereinafter sometimes referred to as a "dextran ladder" or "dextran ladder standard") can be used. The glycan profile obtained from a HILIC/FLR system can be calibrated against the dextran ladder and assigned with glucose unit (GU) values. For example, one such known ladder, the 2AB-labeled dextran calibration ladder, is different than other commercial offerings. The average molecular weight of the glucose homopolymer is higher (~4,500 Dalton), therefore, the "workable" GU value range is twice as much as other dextran ladder standards; the observed GU goes from 2 to 30. Hence, large glycan retention time assignment is improved. The purity and structural integrity of the dextran ladder can be assessed by both HILIC and mass spectrometry ("MS").

The elution times of glycans can be expressed in glucose units ("GU") by reference to the dextran ladder. Each individual glycan structure has a GU value which is directly related to its linkages and constituent monosaccharides. The GU value can be used to predict structures because each monosaccharide in a specific linkage contributes specifically to the GU value of a given glycan. Therefore, the dextran ladders provided herein can be used to calibrate the LC runs against day-to-day or system-to-system changes. The GU value is calculated by fitting a fifth order polynomial distribution curve or cubic spline curve to the dextran ladder, then using this curve to allocate GU values from retention times. The GU values for N-glycans can be very reproducible, with standard deviations being less than 0.3 between columns. This allows direct comparison with database values collected from a range of instruments over a period of time.

Having GU values, databases with glycans stored in values of GU can be interrogated to aid in elucidating the potential glycan structures existing within a glycan population. A dextran ladder also provides a quality controlled standard that can be used to calibrate chromatograms obtained on different instruments in different labs. Glycan retention times captured using HILIC-FLR instrumentation will vary from instrument to instrument and lab to lab. By converting retention times to GU values, the resulting data can be used to compare information between different locations both on-site and off-site. While the use of GU values is used as an example here, other chromatographic methods can benefit from the use of a dextran calibration prepared by the methods of this invention, including but not limited to reversed phase chromatography and mixed mode iterations of both reversed phase and HILIC.

Rapid labeling of N-glycans simplifies preparation of glycan samples for analysis. Yet, it is not a trivial task to produce a dextran ladder that is appropriate for use with glycans that are rapidly labeled with the rapid tagging reagent. Provided herein is a two-step process for tagging of reducing glycans that allows for tuning of chromatographic response and chemical properties, such as fluorescence and MS activity and multiple tags with differing detection properties. Each step differs in the nature of attachment to the reducing glycan. The term "reducing glycan" means reducing sugar, reducing saccharide, reducing polysaccharide (hetero-saccharide different sugar units, or different monosaccharides, or homo-saccharide) and includes any aldehyde terminated saccharide such as chitotriose, chitobiose, galactrose-β-(1-3)-GalNAc-Glycan, mannotrose-di-(N-acetyl-D-glucosamine) and maltrose. A reducing glycan or a reducing sugar is any sugar capable of acting as a reducing agent because it has a free aldehyde group. Hence the methodologies provided herein are useful in tagging or dual tagging of any compound containing an aldehyde (also referred to sometimes as an aldehyde group) including O-glycans.

As shown immediately below, the first step utilizes a reductive amination process comprising the step of reacting a reducing glycan (an aldehyde terminated saccharide) with a compound having a primary amine to produce an intermediate compound such as ethanol amino dextran ladder, propylamino dextran ladder or other compound having an aldehyde that has been converted to a secondary amine, or a reducing glycan (reducing saccharide) converted to be terminated with a secondary amine. Primary amines (also referred to herein as "compound having a primary amine" or amine) which can display a desired characteristic in order to produce the intermediate compound or a compound where its aldehyde is converted to a secondary amine include ethanol amine, propylamine, aminobenzamide, peptides with a free amino terminus (as shown in example 5 herein), N,N-dimethylehtylene diamine, amino anthracene and amino biotin. The second step is a reaction with the rapid tagging reagent that can impart differing properties. In other words, characteristics of the intermediate compound are different from the rapid tagged compound (i.e., rapid tagged glycan).

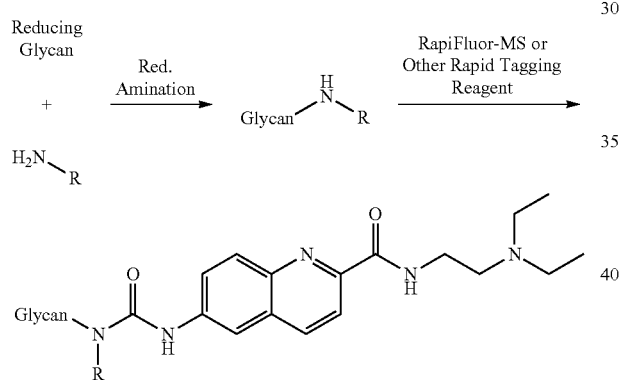

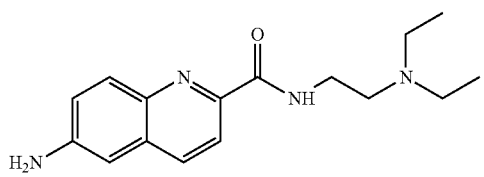 [SMILES: CCN(CC)CCNC(=O)c1ccc2cc(N)ccc2n1]

Where R—NH$_2$ is ethanol amine or similar type of compound having a primary amine.

Figure 2:
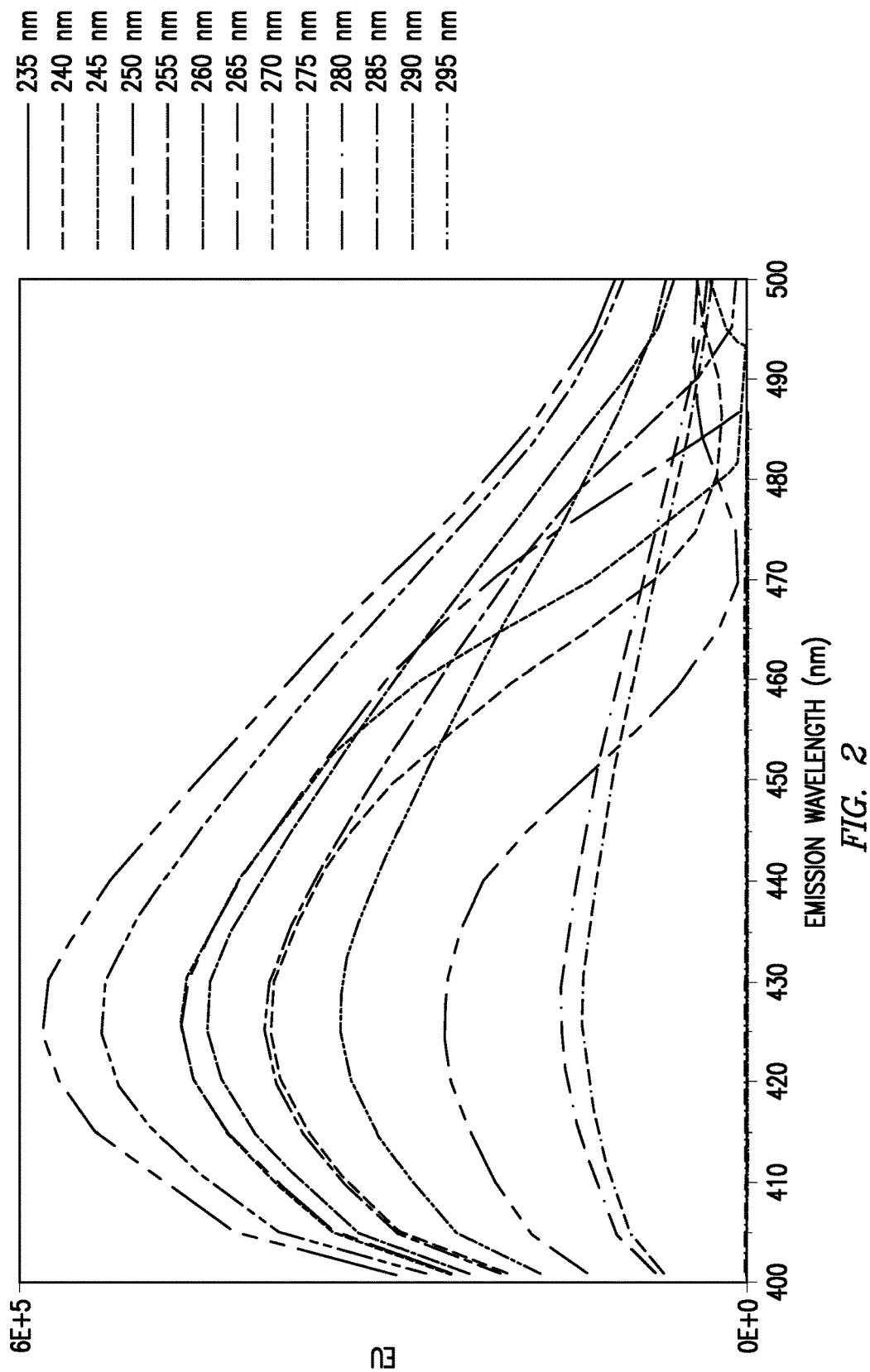
FIG. 2 shows fluorescence emission spectra for a rapid labeled N-glycan labeled with a rapid tagging reagent having optimized wavelengths of 265 nm for excitation and 425 nm for emission.
Figure 3:
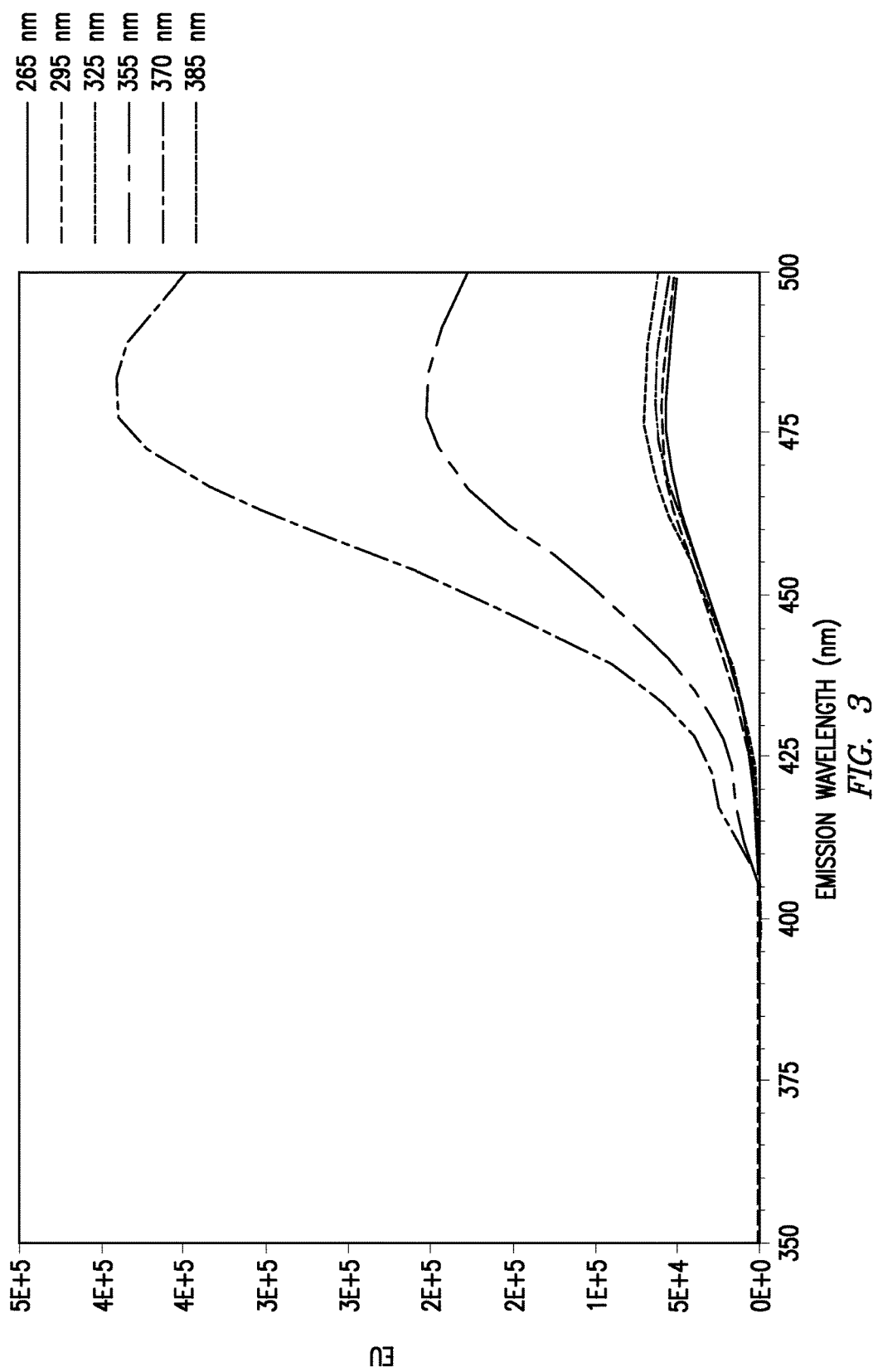
FIG. 3 shows fluorescence emission spectra for a dextran ladder labeled with analog of a rapid tagging reagent by reductive amination only having shifted fluorescence properties of optimized wavelengths of 370 nm for excitation and 480 nm for emission.

This methodology initially arose out of a need to match optical properties between N-linked glycans tagged with the rapid tagging reagent (FIG. 2) to the properties of a dextran standard (also referred to herein as a reducing sugar) (FIG. 3) tagged via only reductive amination using a precursor as shown immediately below:

Between these two material types, it was found that fluorescence properties, namely excitation and emission maxima, are disadvantageously different. As a consequence, such a dextran ladder was not a suitable calibrant for the analysis of rapid labeled glycans in liquid chromatography.

The methodologies provided herein utilize a reaction route to tagging of reducing glycans (or any glycan that is aldehyde terminated) with a rapid tagging/amine reactive label to provide detection of the N glycan through its fluorescent and/or MS active properties. Traditional tagging of reducing glycans involves reductive amination (a lengthy process, i.e., 1 to 4 hours and possibly as long as 8 hours for high yield) with a specific tagging reagent. While, the present methodologies utilize reductive amination, once the intermediary amine is produced, a second step (fast, ~5 min) is taken to introduce the tag (or label) having the fluorescent/MS active properties and provide saccharide molecules of the following structure Formula I. As provided in this embodiment, the terminal monosaccharide residue is shown to be an N-acetylated glucosamine (GlcNAc) that is linked to the remaining saccharide structure through its 4-OH position. The terminal monosaccharide residue does not have to be a GlcNAc, however; the dextran ladder can be terminated with a glucose monosaccharide that links to the structure through its 6-OH position. In addition, the terminal monosaccharide residue can be linked through the 4-OH position. The dextran ladder can be terminated with any glucose monosaccharide that links to the remaining saccharide structure through its 6-OH position as exemplified in Formula II below.

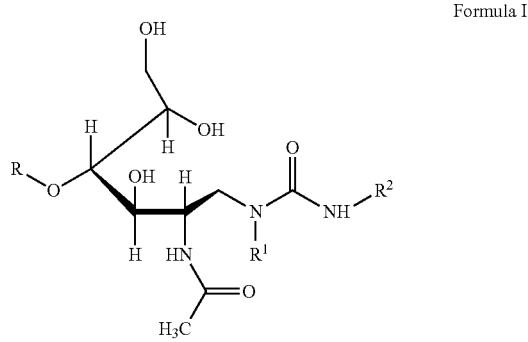

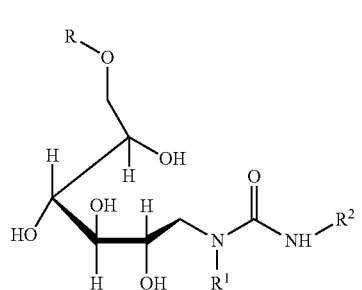

where R can be monosaccharide units or glucose residues, R$_1$ is —CH$_2$CH$_2$OH and R$_2$ is the portion of the rapid tagging reagent which incorporates the FLR-MS functionality into the structure, and is exemplified with the following structures:

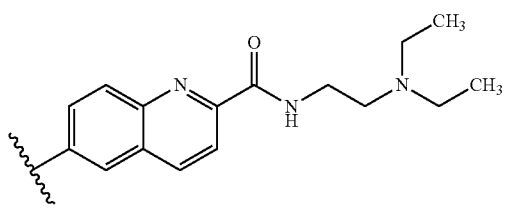

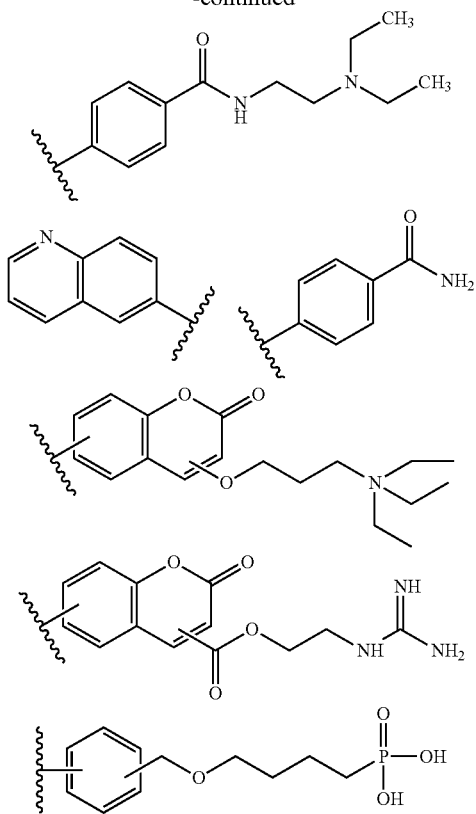

The methodologies provided herein allow for tagging of reducing glycans with the rapid tagging agent which has the same optical and MS properties as other molecules that have been labeled with the rapid tagging reagent. In other words, carrying out reductive amination with the primary amine of the rapid tagging reagent can produce a molecule that differs in absorbance and emission properties from comparable molecules labeled with the rapid tagging agent (N-linked molecules). The linkers can be different (amine vs urea), resulting in changes in chromophore properties. By carrying out reductive amination with a compound having a primary amine, then tagging the amine with the rapid tagging reagent, the optical properties are maintained.

Figure 4A:
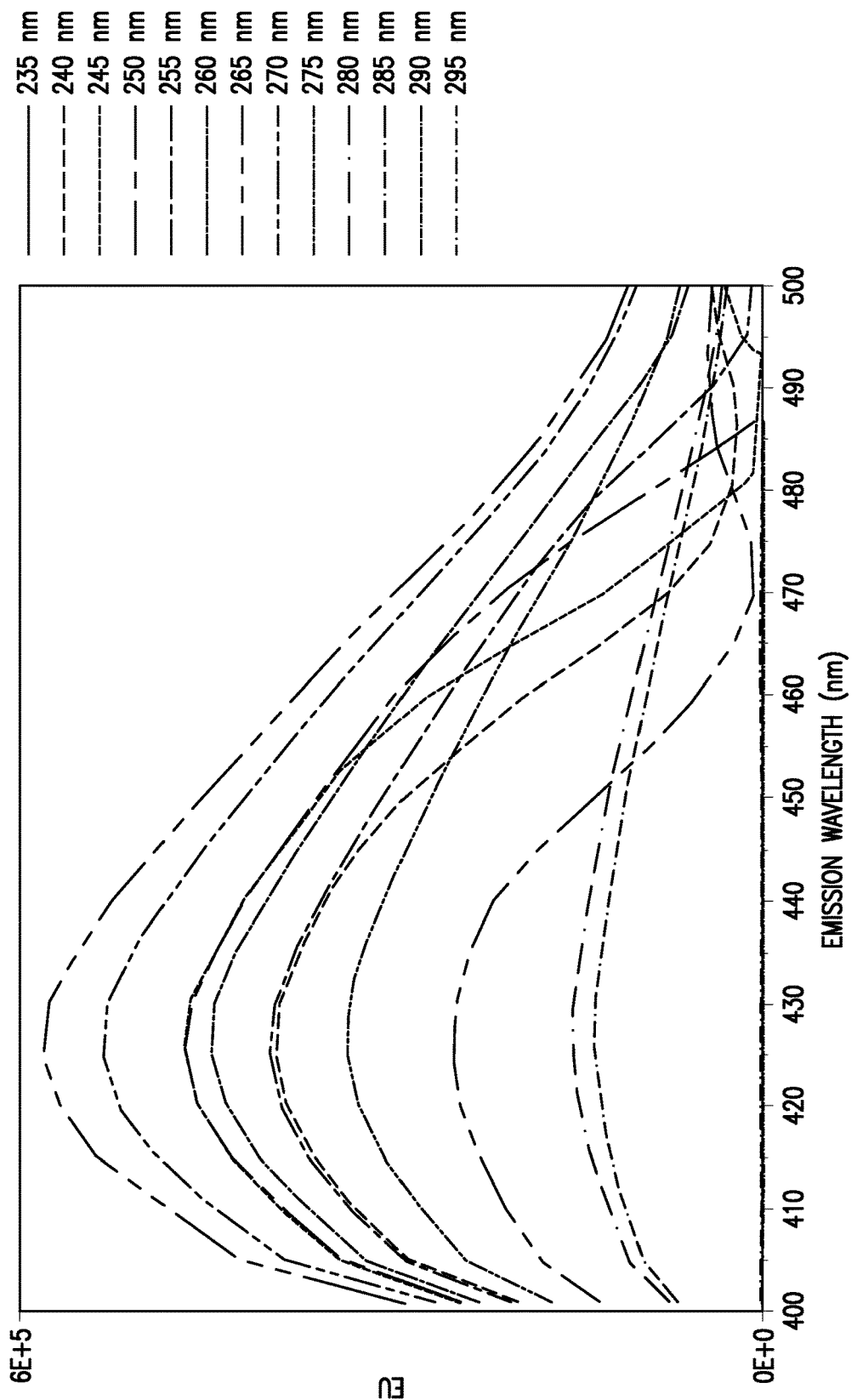
FIGS. 4A and 4B show fluorescent properties of a rapid labeled dextran ladder produced with the methods provided herein.

FIG. 4A show optical properties of the rapid labeled dextran ladder produced by the methods described herein where the rapid tagging reagent is:

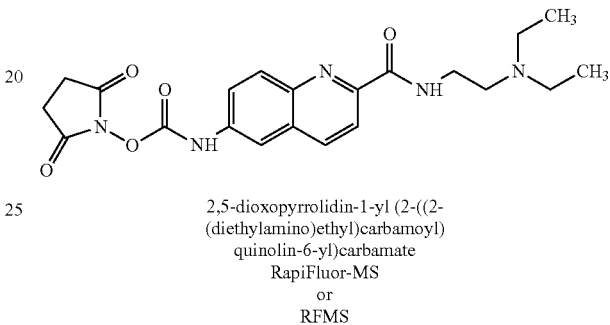

Figure 4B:
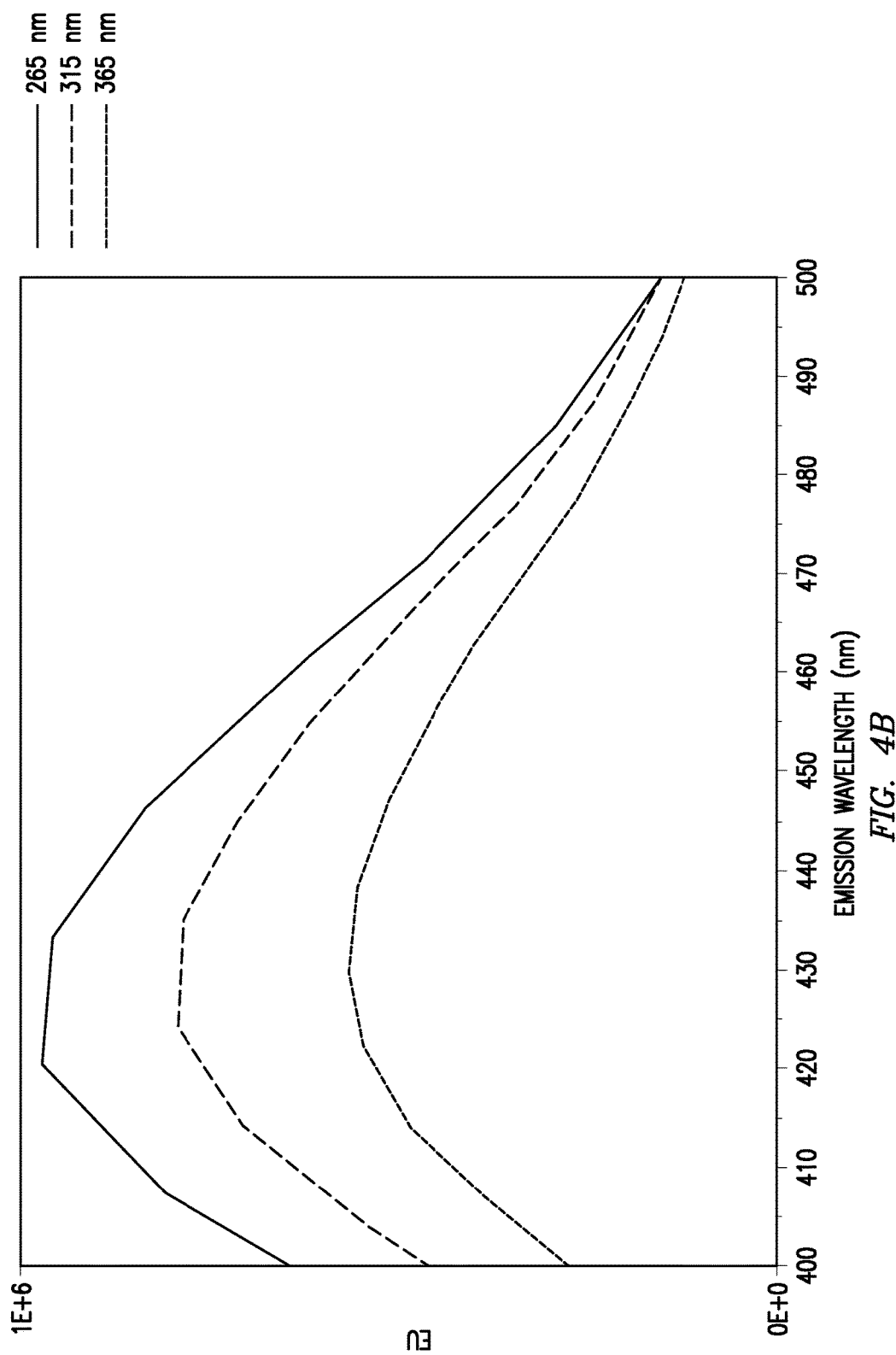

2,5-dioxopyrrolidin-1-yl (2-((2-(diethylamino)ethyl)carbamoyl)quinolin-6-yl)carbamate
RapiFluor-MS
or
RFMS FIG. 4B shows that the dextran ladder has substantially identical fluorescence properties as that of the rapid labeled glycan produced with the same rapid tagging reagent, the rapid labeled glycan which is exemplified below:

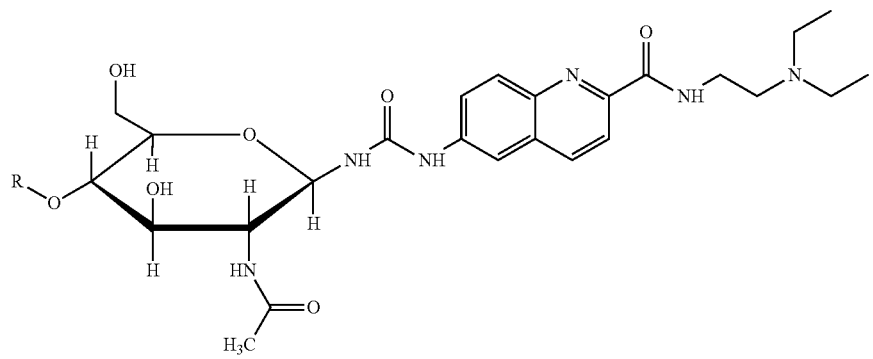

A Rapid Labeled Glycan

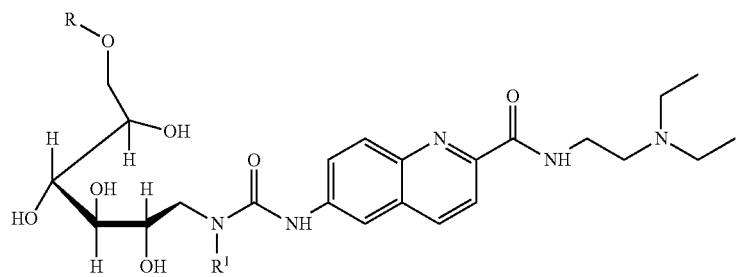

A Rapid Labeled Dextran Ladder

The present methodologies allow for adjusting the relative retention of a glucose homopolymer (referred to herein as a "dextran ladder") through changes in overall polarity. For example, tagging of the dextran ladder through reductive amination with a) ethanolamine or b) propylamine, followed by reaction with the rapid tagging reagent, results in differing retention characteristics. Thus, the chromatographic retention characteristics, among other characteristics, of the dextran ladder can be tuned as a calibration standard.

Accordingly, the present methodologies can produce a dextran ladder having chemical properties highly similar to those of N-glycans that are labeled with a rapid tagging labeling reagent.

As provided in the proposed procedures set out in Example 3, one embodiment of such a glucose homopolymer includes reductive amination with ethanolamine followed by labeling with the rapid tagging reagent to produce a rapid labeled ethanolamino dextran ladder (an embodiment of a rapid labeled dextran ladder) shown immediately below:

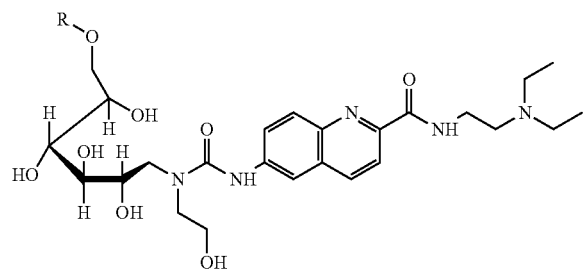

Figure 7A:
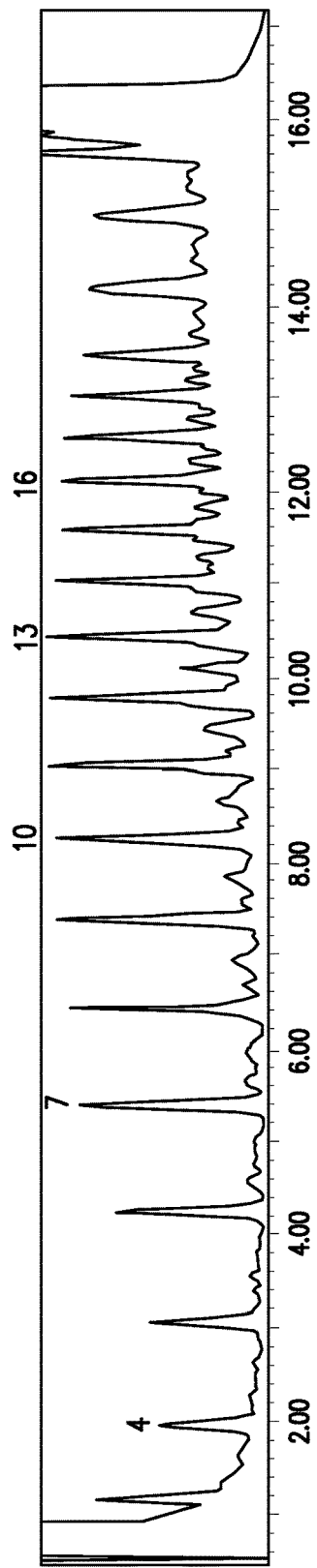
FIGS. 7A and 7B show the fluorescence chromatogram obtained for a rapid labeled, propylamino dextran versus a rapid labeled ethanolamino dextran using a glycan BEH amide 2.1×50 mm column.

In another embodiment, the ethanolamine in the procedures set out in Example 3 can be replaced with propylamine. The resulting rapid labeled propylamino dextran (shown below) exhibits altered chromatographic retention when separated with a BEH Amide stationary phase as shown in FIG. 7A versus that shown in FIG. 7B.

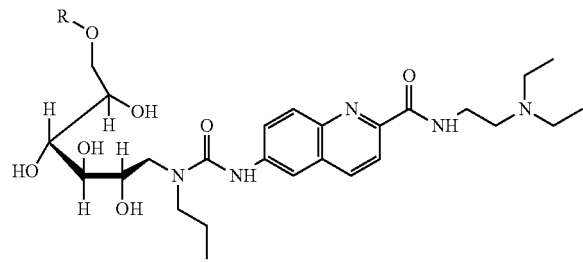

Rapid Labeled Propylamino Dextran, a Rapid Labeled Dextran Ladder

Example 2

Preparation of the Rapid Labeled Dextran Ladder

Reductive Amination of Dextran, Coupling Procedure 100 mg of Dextran 5000 is accurately weighed and placed in an 8 mL. 2800 µl of DMSO is then piped into the 8 mL vial and stirred until the dextran is dissolved. The actual weight is then recorded.

Add 1200 µl of glacial acid to the 8 ml vial followed by 90.0 mg (91.0 ml) of redistilled ethanolamine (MW=61.08, d=1.012) and then add 128 mg of sodium cyanoborohydride. Gently mix the slurry and incubate for 3 hours at 70° C. in a heat block with magnetic stirring. Following the 3 hour incubation, the resulting reaction is removed from the heat block and cooled to a temperature below 40° C. Transfer the reaction contents from the 8 ml vial into a tared 50 ml centrifuge and add 40 ml of ACN. Measure and Record the Tare Weight, and place the vial in a refrigerator for 30 minutes. Then, centrifuged the mixture at 4000 RPM for 5 minutes and decant the supernatant. Re-suspend the pellet in 40 ml ACN and vortex vigorously. Repeat the steps of centrifugation, decantation and re-suspension for a total of three washes. The 30 minute stand is not required. Dry the pellet under a stream of nitrogen for 20 minutes and then overnight under vacuum at room temperature. Weigh the pellet to determine final recovery. Record the Final weight, Tare Weight and Recovered Weight.

Procedure for Rapid Labeling to Produce the Ethanolamino Labeled Dextran Ladder

This procedure is designed for the rapid tagging reaction to be performed at a 100-200 fold molar excess of the rapid tagging reagent. Dissolve 4.0±0.3 mg of the ethanolamino dextran in 500 µl of 50 mM HEPES, pH 7.9 (titrated from free acid with sodium hydroxide). Add 300 µl of anhydrous DMF. Use this dextran solution to dissolve 100±0.5 mg of rapid tagging reagent. Allow the reaction to proceed at room temperature for 10 minutes. Periodically (every 20 to 30 seconds), stir/agitate the reaction mixture. At the completion of the incubation at room temperature, dilute the reaction with 7.6 ml ACN. A best practice is to dilute the reaction right before loading onto the SPE cartridge.

HILIC SPE Clean-Up

Wash with 6 ml of water and 6 ml equilibration with 85% ACN. Load the ACN diluted reaction mixture in two (2) 4.5 ml volumes (approximate volume) onto a cartridge. Washed three times 6 ml volumes of 1:9:90 formic acid/water/ACN. Elute with three (3) 4 ml volumes of 200 mM ammonium acetate without pH adjustment, 5% ACN. Dispense 600 µl volumes and dry via centrifugal vacuum evaporation.

The above procedure can result in yields of the labeled dextran ladder prepared from ethanolamino dextran intermediate up to about 80 standards per batch.

Example 3

Experimental Conditions and Representative Data for Rapid Labeled Ethanolamino Dextran, a Rapid Labeled Dextran Experimental Conditions for Batches 1 to 3 of rapid labeled Ethanolamino Dextran, a Rapid Labeled Dextran-Liquid chromatography was used to analyze the fluorescence and MS properties of the labeled dextran ladder as prepared in Example 2. The column was flushed in 70% HPLC grade acetonitrile (ACN)/30% HPLC grade water v/v. The column was then equilibrated with mobile phase conditions before making first injection. Table 2 and Table 3 immediately below provide HILIC UPLC/FLR/MS conditions used in the analysis.

TABLE 2

| | | | | | |
|---|---|---|---|---|---|
| System | ACQUITY UPLC ® H-Class Bio System with an ACQUITY UPLC ® FLR Detector/Synapt G2-S | | | | |
| Column | ACQUITY UPLC ® Glycan BEH Amide, 130 Å, 1.7 µm, 2.1 × 150 mm | | | | |
| Temperature | 60° C. | | | | |
| Mobile Phase A | 50 mM Ammonium Formate, pH 4.5 | | | | |
| Mobile Phase B | 100% acetonitrile (ACN) | | | | |
| Flow Rate | 0.4 mL/min | | | | |

| Gradient | Time (min) | Flow Rate (mL/min) | % A | % B | Curve |
|---|---|---|---|---|---|
| | 0.0 | 0.4 | 25 | 75 | 6 |
| | 40.0 | 0.4 | 49 | 51 | 6 |
| | 41.5 | 0.2 | 100 | 0 | 6 |
| | 44.5 | 0.2 | 100 | 0 | 6 |
| | 48.1 | 0.2 | 25 | 75 | 6 |
| | 52.6 | 0.4 | 25 | 75 | 6 |
| | 60.0 | 0.4 | 25 | 75 | 6 |

| | |
|---|---|
| FLR wavelength | EX 265/EM 425 nm |
| FLR sampling rate | 2 Hz |
| Injection volume | 1 µL |

TABLE 3

Mass Spectrometry

| | |
|---|---|
| Capillary | 3.0 Kv |
| Cone | 80 V |
| Source offset | 50 V |
| Extraction cone | 4 V |
| Desolvation gas | 800 L/hr |
| Nebulizer | 6 bar |
| Source Temperature | 120° C. |
| Desolvation Temperature | 350° C. |
| Sampling Rate | 1 Hz |
| Flow Rate | 5 µL/min |
| Acquisition Rate | 100-2500 m/z |
| LockMass Calibration | 0.1 µM Glu-fibrinopeptide B in 50:50 water/ACN, 0.1% (v/v) FA (real-time mass correction) |

Figure 5A:
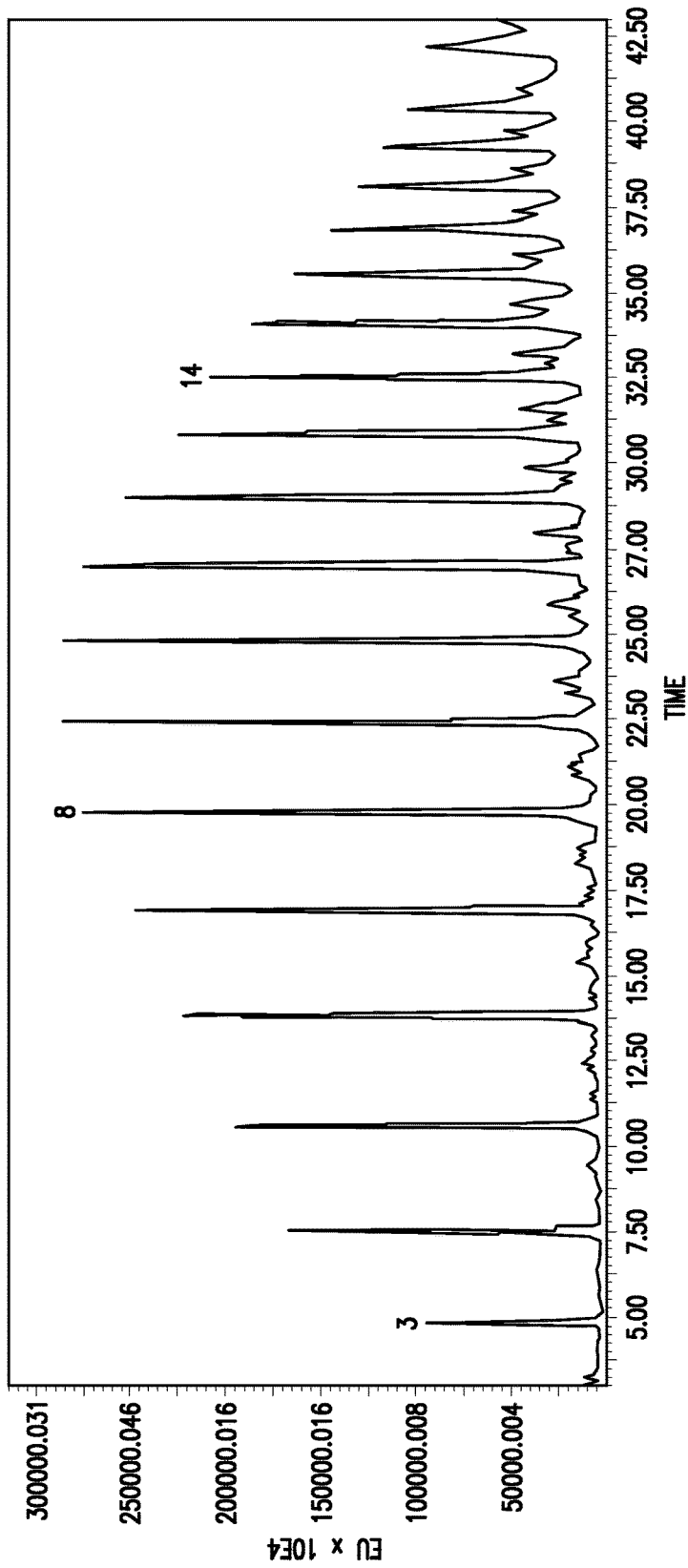
FIGS. 5A, 5B and 5C show representative HILIC fluorescence chromatograms for a rapid labeled ethanolamino dextran ladder produced via the methods provided herein.
Figure 5B:
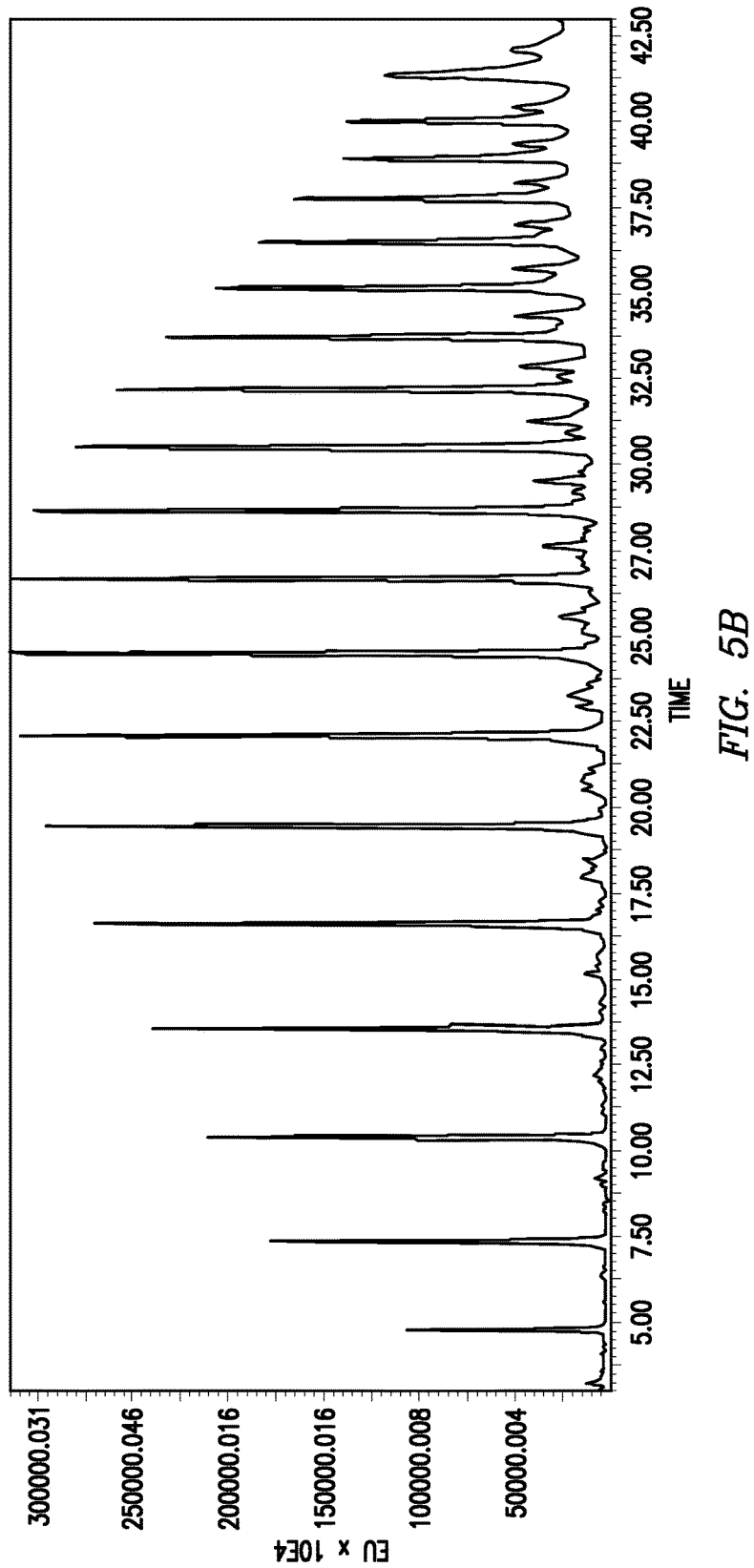
Figure 5C:
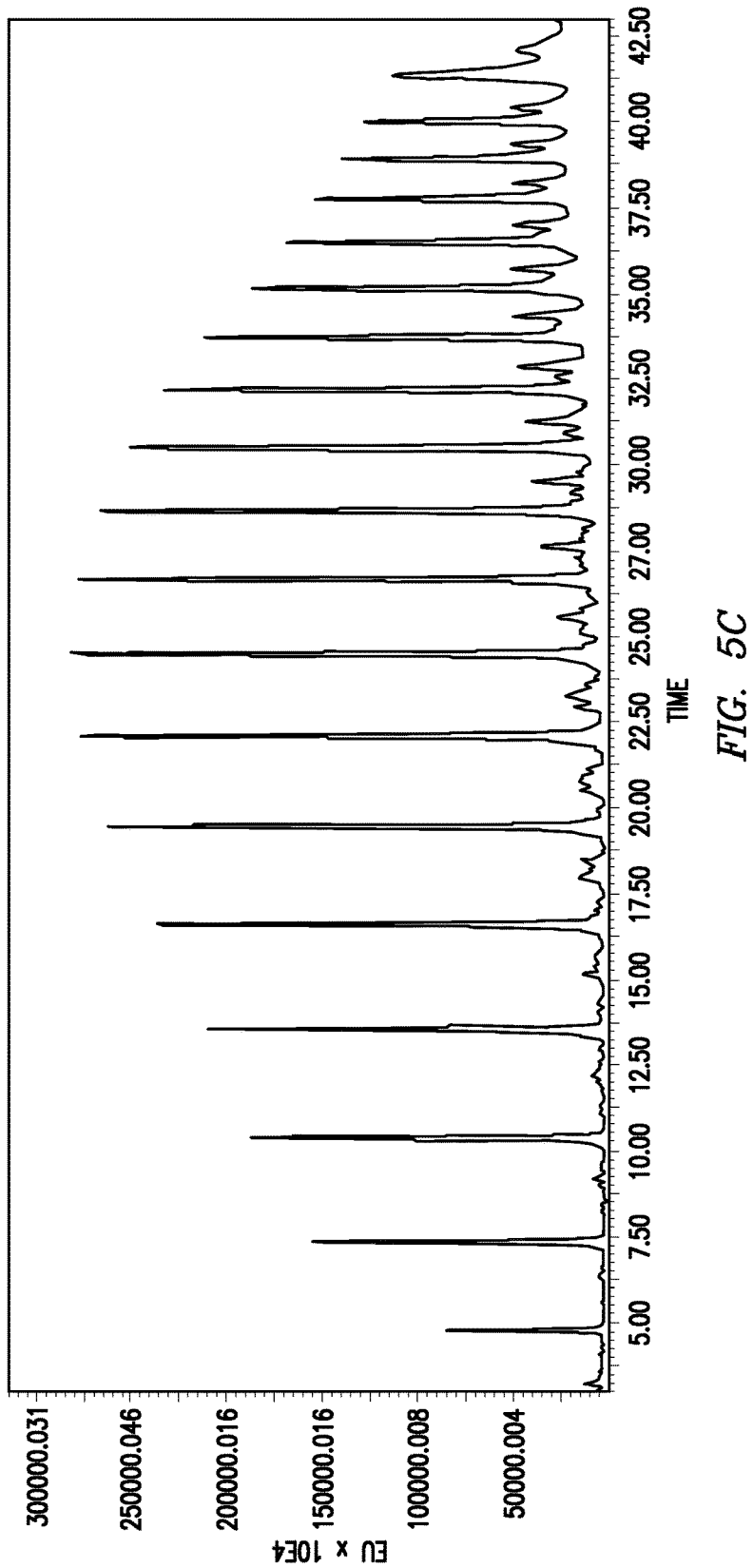
Figure 6A:
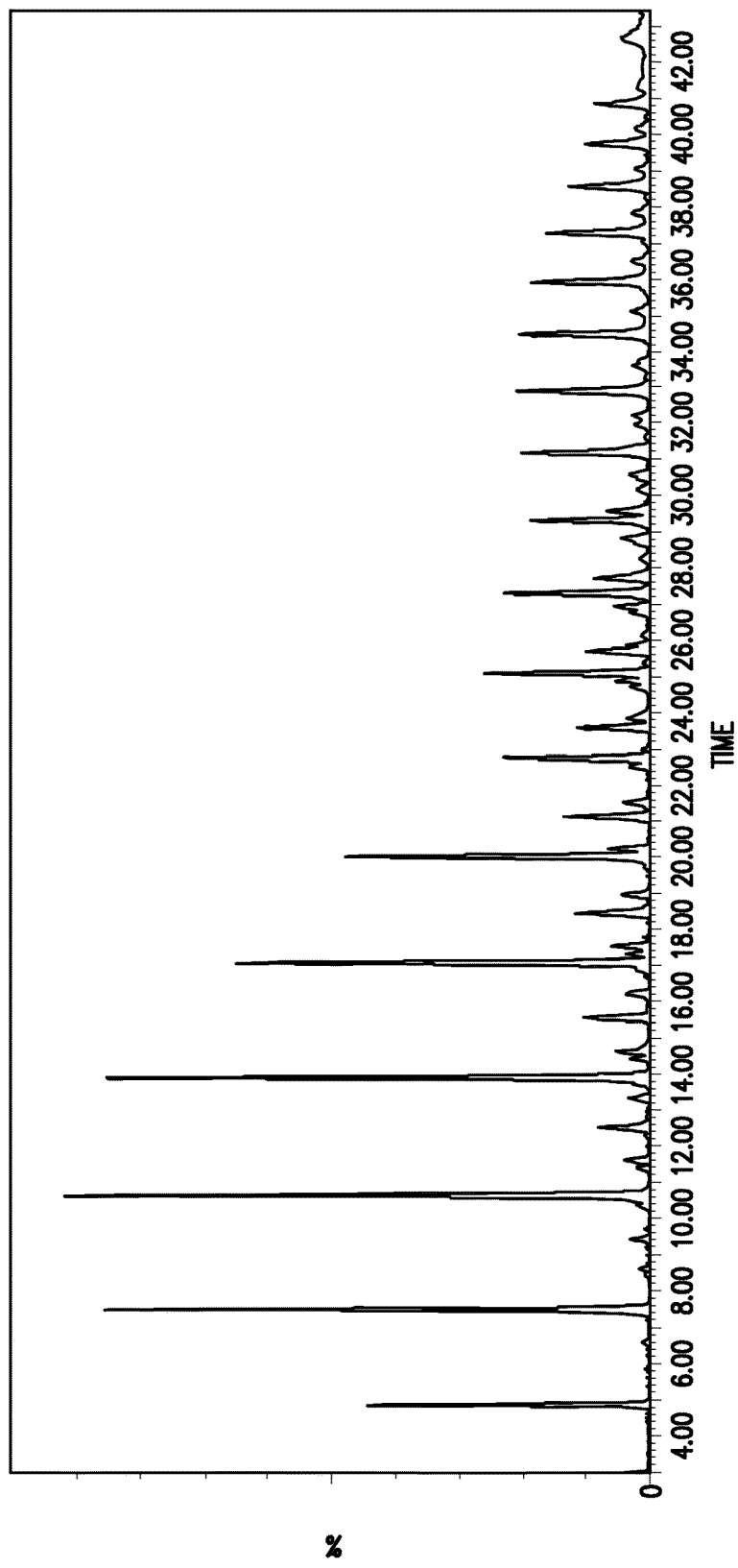
FIGS. 6A, 6B and 6C show the corresponding Base Peak Ion ("BPI") chromatograms for each batch of the rapid labeled dextran ladders of Example 3.
Figure 6B:
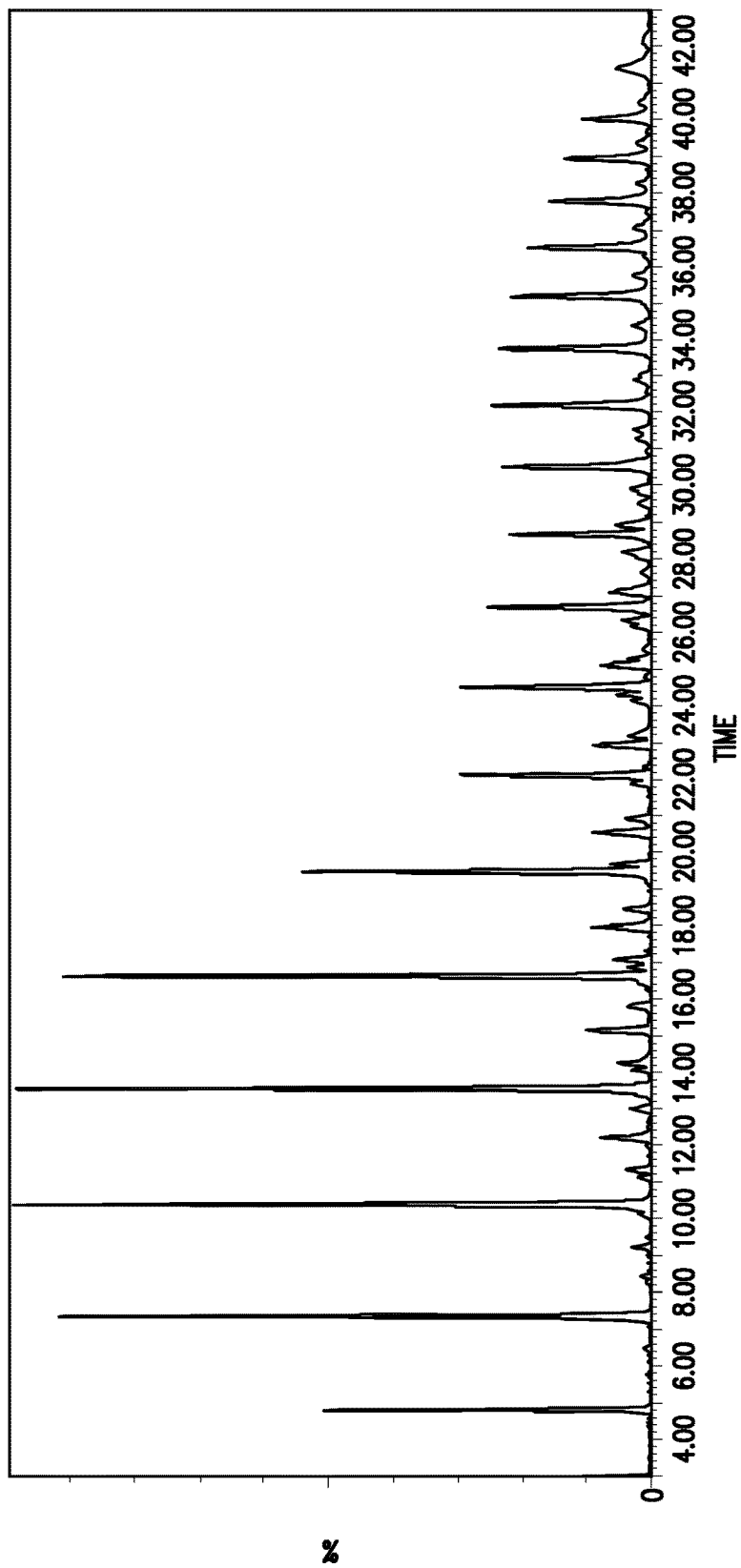
Figure 6C:
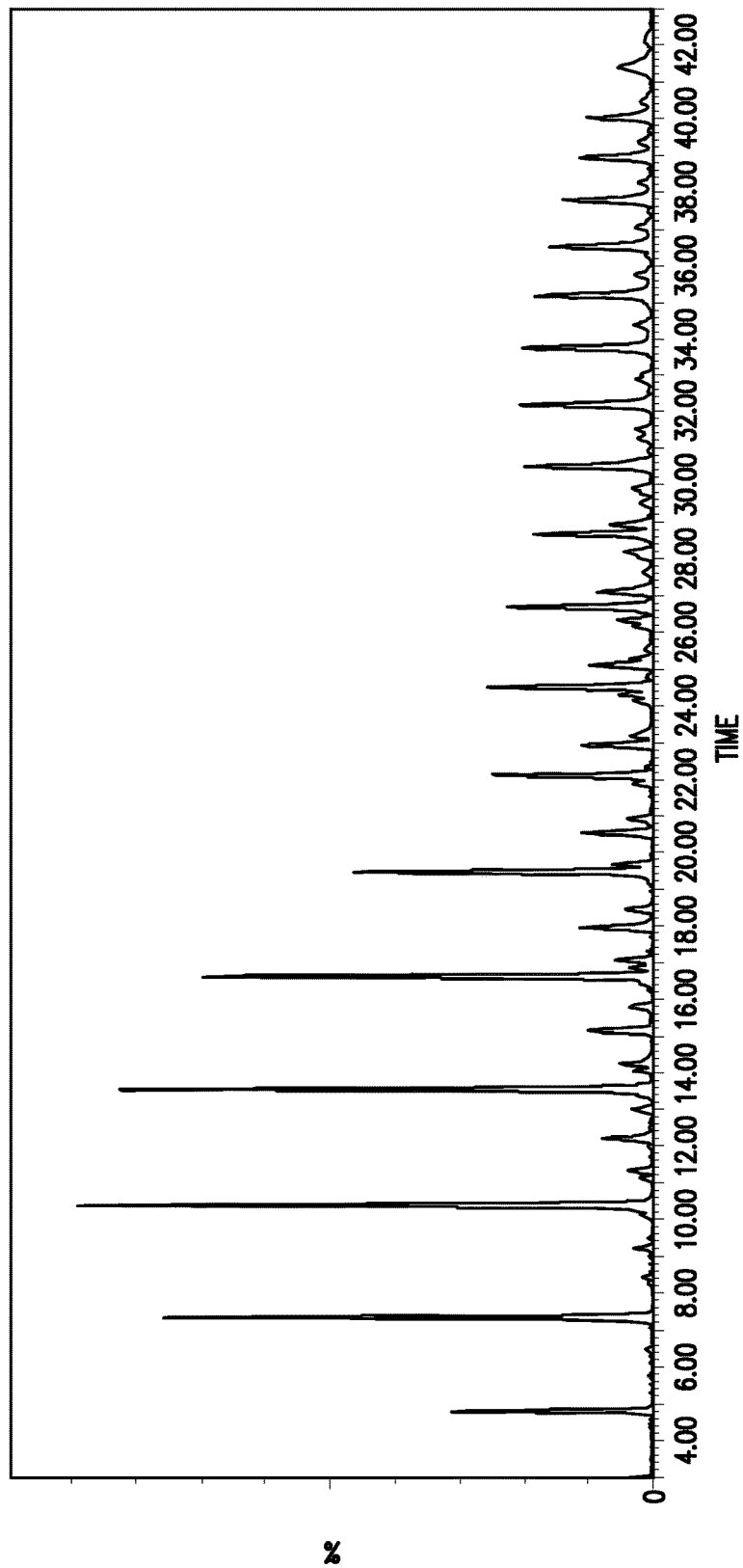

FIGS. 5A, 5B and 5C show the fluorescence chromatograms for each of the three batches of the labeled (ethanolamino) dextran ladder prepared. FIGS. 6A, 6B and 6C show the corresponding Base Peak Ion (BPI) chromatograms for each batch of rapid labeled dextran ladder. The masses of labeled Glucose Units (GU) species are shown in Table 4.

TABLE 4

| GU | Labeled Dextran Ladder | m/z (monoisotropic) [M + H]+ | m/z (monoisotropic) [M + 2H]2+ |
|---|---|---|---|
| 2 | 699.333 | 700.340 | 350.674 |
| 3 | 861.391 | 862.398 | 431.703 |
| 4 | 1023.449 | 1024.456 | 512.732 |
| 5 | 1185.507 | 1186.514 | 593.761 |
| 6 | 1347.565 | 1348.572 | 674.790 |
| 7 | 1509.623 | 1510.630 | 755.819 |
| 8 | 1671.681 | 1672.688 | 836.848 |
| 9 | 1833.739 | 1834.746 | 917.877 |
| 10 | 1995.797 | 1996.804 | 998.906 |
| 11 | 2157.855 | 2158.862 | 1079.935 |
| 12 | 2319.913 | 2320.920 | 1160.964 |
| 13 | 2481.971 | 2482.978 | 1241.993 |
| 14 | 2644.029 | 2645.036 | 1323.022 |
| 15 | 2806.087 | 2807.094 | 1404.051 |
| 16 | 2968.145 | 2969.152 | 1485.080 |
| 17 | 3130.203 | 3131.210 | 1566.109 |
| 18 | 3292.261 | 3293.268 | 1647.138 |
| 19 | 3454.319 | 3455.326 | 1728.167 |
| 20 | 3616.377 | 3617.384 | 1809.196 |

Example 4

Modulating Chromatographic Retention with the Compound Having Primary Amine Via Reductive Amination A second rapid labeled dextran was prepared by replacing ethanolamine set out in EXAMPLE 2 with propylamine. The chromatographic retention of the resulting rapid labeled, propylamino dextran was compared with that of the previously mentioned rapid labeled, ethanolamino dextran according to the experimental conditions outlined below:

The column was flushed in 70% HPLC grade acetonitrile (ACN)/30% HPLC grade water v/v. The column was then equilibrated with mobile phase conditions before making first injection. Table 5 provides the HILIC UPLC/FLR conditions used in the analysis.

TABLE 5

| | | | | | |
|---|---|---|---|---|---|
| System | ACQUITY UPLC ® H-Class Bio System with an ACQUITY UPLC ® FLR Detector | | | | |
| Column | ACQUITY UPLC ® Glycan BEH Amide, 130 Å, 1.7 µm, 2.1 × 50 mm | | | | |
| Temperature | 60° C. | | | | |
| Mobile Phase A | 50 mM Ammonium Formate, pH 4.5 | | | | |
| Mobile Phase B | 100% acetonitrile (ACN) | | | | |
| Flow Rate | 0.4 mL/min | | | | |

| Gradient | Time (min) | Flow Rate (mL/min) | % A | % B | Curve |
|---|---|---|---|---|---|
| | 0.0 | 0.4 | 25 | 75 | 6 |
| | 40.0 | 0.4 | 49 | 51 | 6 |
| | 41.5 | 0.2 | 100 | 0 | 6 |
| | 44.5 | 0.2 | 100 | 0 | 6 |
| | 48.1 | 0.2 | 25 | 75 | 6 |
| | 52.6 | 0.4 | 25 | 75 | 6 |
| | 60.0 | 0.4 | 25 | 75 | 6 |

| | |
|---|---|
| FLR wavelength | EX 265/EM 425 nm |
| FLR sampling rate | 10 Hz |
| Injection volume | 1 µL |

Figure 7B:
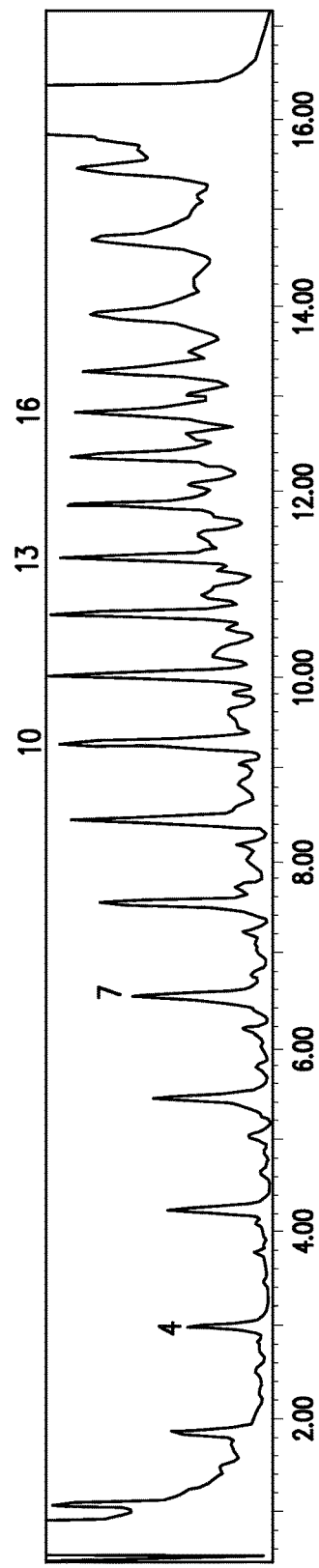

FIGS. 7A and 7B show the fluorescence chromatogram obtained for rapid labeled, propylamino dextran versus rapid labeled ethanolamino dextran when using a BEH Amide 2.1×50 mm column.

Prophetic Example 5

Incorporating Multiple Functionalities Onto A Reducing Saccharide

More broadly, the presented methodology can impart certain chemical properties onto reducing glycans and sugars via incorporation of separate labeling moieties (or also referred to herein as "tags" or "labels"), one via reductive amination and another by rapid tagging processing.

In an embodiment of the present methodologies, a twice labeled N-glycan can be purified from sample matrices via streptavidin pull-down and then subsequently detected via the rapid tagging reagent to impart fluorescence and/or enhanced ionization efficiency. This "twice-labeled" saccharide shown below can have a biotin label along with a highly fluorescent, MS active label. In an embodiment shown immediately below, an amino biotin molecule could be used for reductive amination and the reductively aminated saccharide could be labeled via a rapid tagging reaction.

Rapid Labeled Benzamide Amino Saccharide

The present methodology could also allow saccharides/glycans to be labeled with an epitope tag such that immunoaffinity enrichment or immuno based detection is enabled. In one particular embodiment, a saccharide can be reductively aminated with a hemagglutinin (HA) epitope tag, a peptide of sequence YPYDVPDYA, and then labeled with the rapid tagging reagent.

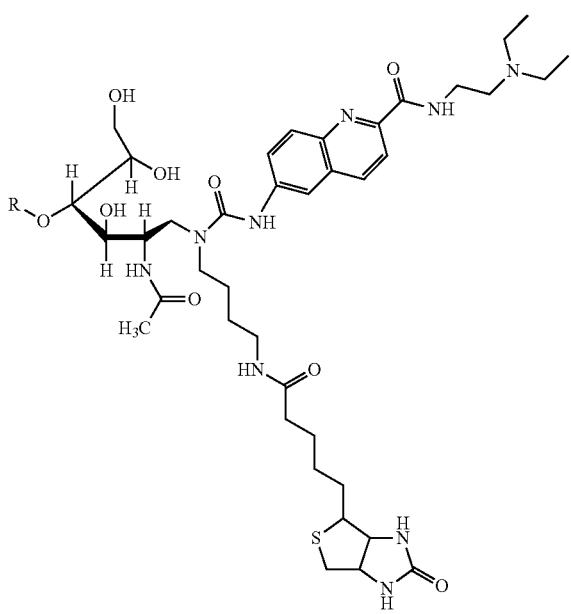

Rapid Labeled, Biotinylated Saccharide

In an embodiment, more than one fluorophore/chromophore can be used to enable multiple wavelength detection on a single saccharide species, as would be possible if this methodology was applied to reductively aminate a glycan with aminobenzamide and to thereafter label it with the rapid tagging reagent.

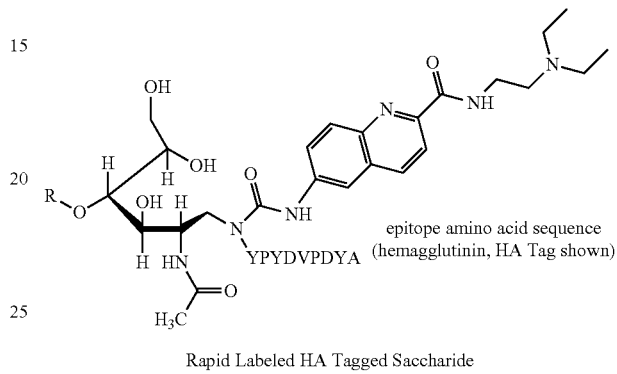

Rapid Labeled HA Tagged Saccharide

We claim:

1. A calibrant of the structural formula:

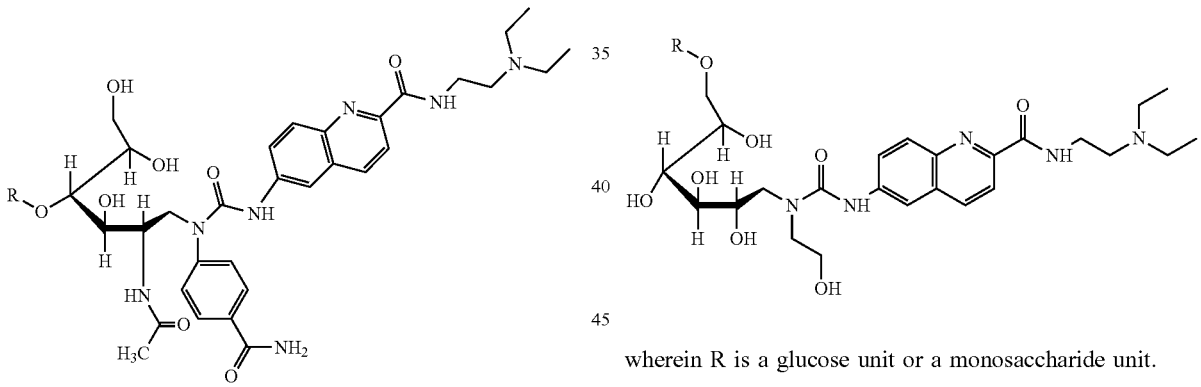

wherein R is a glucose unit or a monosaccharide unit.

* * * * *